United States Patent
Halstead et al.

(10) Patent No.: US 6,919,057 B2
(45) Date of Patent: Jul. 19, 2005

(54) AUTOMATED ENDOSCOPE REPROCESSOR

(75) Inventors: Éric Halstead, Beauport (CA); Eugéne Cantin, St-Jean-Chrysostôme (CA); Michel Trachy, Beauport (CA); Christian Angers, Ancienne-Lorette (CA); Serge Coulombe, Boischatel (CA); Maxime Nicole, St-Pacome (CA)

(73) Assignee: Steris Inc., Temecula, CA (US)

( * ) Notice: Subject to any disclaimer, the term of this patent is extended or adjusted under 35 U.S.C. 154(b) by 481 days.

(21) Appl. No.: 10/115,847

(22) Filed: Apr. 4, 2002

(65) Prior Publication Data

US 2003/0190256 A1 Oct. 9, 2003

(51) Int. Cl.[7] .............................................. A61L 2/00
(52) U.S. Cl. ................... 422/297; 422/1; 422/3; 422/28; 422/29; 422/33; 422/62; 422/300
(58) Field of Search ........................... 422/1, 3, 28, 29, 422/33, 297, 300, 62; 436/2, 1, 26; 435/31, 287.4

(56) References Cited

U.S. PATENT DOCUMENTS

| | | | |
|---|---|---|---|
| 4,731,222 A | | 3/1988 | Kralovic et al. |
| 4,943,414 A | | 7/1990 | Jacobs et al. |
| 5,288,467 A | | 2/1994 | Biermaier .................... 422/116 |
| 5,494,530 A | | 2/1996 | Graf |
| 5,551,462 A | | 9/1996 | Biermaier |
| 5,580,530 A | | 12/1996 | Kowatsch et al. |
| 5,641,464 A | | 6/1997 | Briggs, III et al. |
| 5,711,921 A | | 1/1998 | Langford |
| 5,736,355 A | * | 4/1998 | Dyke et al. .................... 435/31 |
| 5,749,385 A | | 5/1998 | Rochette et al. |
| 5,753,195 A | | 5/1998 | Langford et al. |
| 5,833,935 A | * | 11/1998 | Malchesky ................... 422/300 |
| 5,840,251 A | | 11/1998 | Iwaki |
| 5,846,484 A | * | 12/1998 | Scarborough et al. ......... 422/28 |
| 5,858,305 A | * | 1/1999 | Malchesky .................... 422/28 |
| 5,871,692 A | | 2/1999 | Haire et al. |
| 5,906,802 A | | 5/1999 | Langford |
| 5,928,948 A | * | 7/1999 | Malchesky ...................... 436/2 |
| 6,013,227 A | | 1/2000 | Lin et al. |
| 6,027,572 A | | 2/2000 | Labib et al. |
| 6,066,294 A | | 5/2000 | Lin et al. |
| 6,068,815 A | | 5/2000 | Oberleitner et al. |
| 6,193,931 B1 | * | 2/2001 | Lin et al. ...................... 422/28 |
| 6,354,312 B1 | | 3/2002 | Lin et al. ................. 134/169 C |
| 2002/0001537 A1 | | 1/2002 | Hlebovy et al. .............. 422/28 |

OTHER PUBLICATIONS

"Chemical–Thermal Disinfection", INNOVA 2000 reliable automatic disinfection of endoscopes. BHT–INNOVA 2000.

* cited by examiner

*Primary Examiner*—Krisanne Jastrzab
(74) *Attorney, Agent, or Firm*—Fay, Sharpe, Fagan, Minnich & McKee, LLP

(57) ABSTRACT

An automated endoscope reprocessor (10) includes a removable rack (12) for receiving a container (16, 16'). The container has a clamshell housing (20) having two mating portions (24, 26). The portions together define an internal pressurizable chamber (56) for receiving an endoscope head (22). The endoscope's connector cord (82) is carried through an outlet (80) to the chamber. The outlet is defined by channels (88, 90), one in each of the two housing portions (24, 26). A gasket assembly in the outlet provides a restricted fluid passage which allows a small portion of fluid to flow through the outlet when the connector cord is positioned therein. The gasket assembly (120) includes a number of resiliently flexible fins (126, 128, 130) positioned in each channel, each fin having a U-shaped slot (144, 146, 148). Pairs of fins overlap such that the slots together define openings (150) of diminishing size. Depending on the diameter of the cord, the cord is contacted by one or more of the fins adjacent the respective slot. A reprocessing liquid, such as peracetic acid in solution, is pumped into the chamber (56). The liquid leaks slowly through the slots, allowing an above ambient pressure to be maintained in the chamber, while ensuring that all exterior surfaces of the endoscope are contacted with the reprocessing liquid.

36 Claims, 18 Drawing Sheets

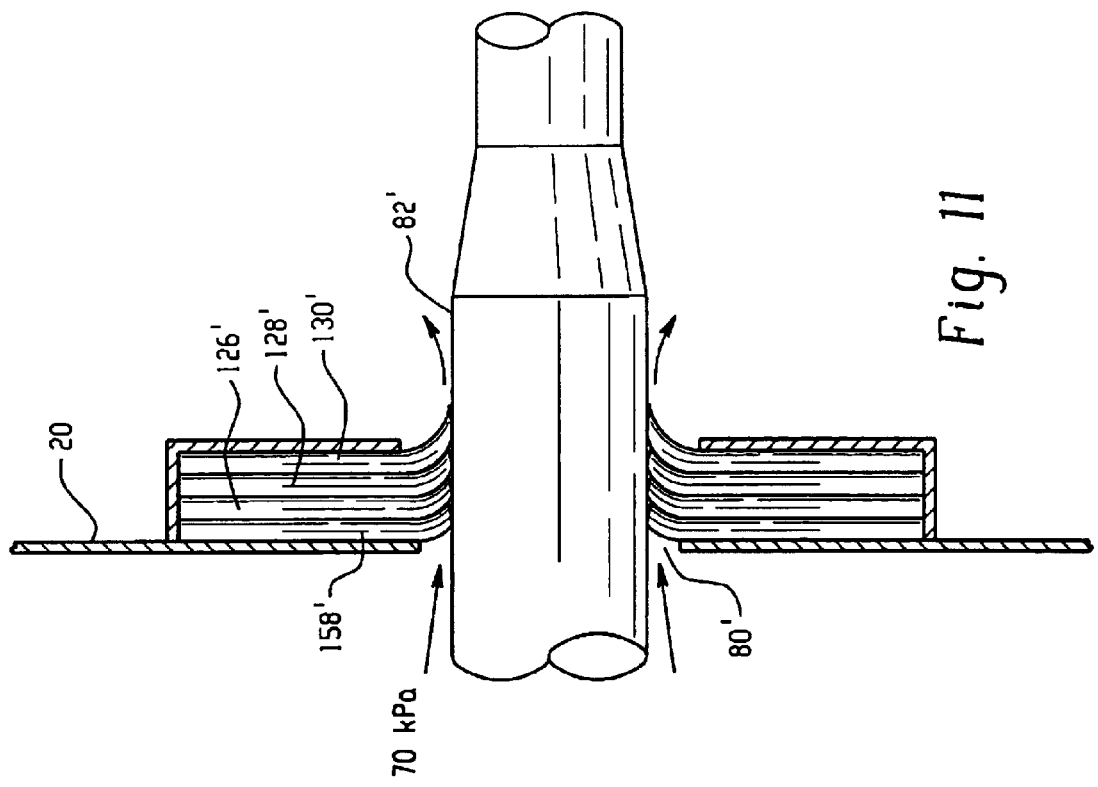
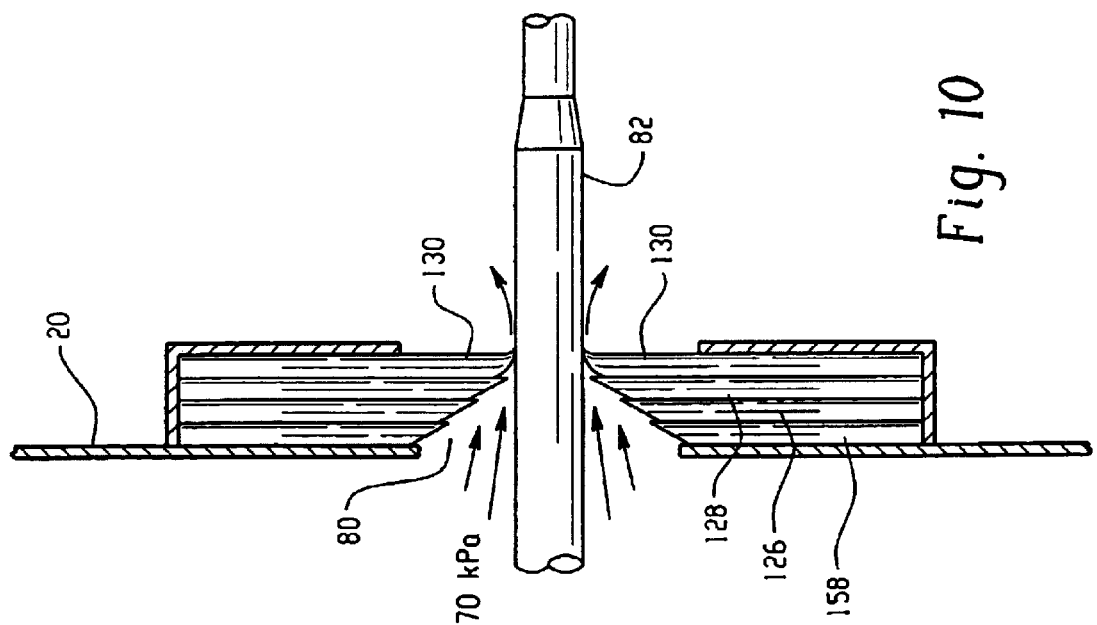

AUTOMATED ENDOSCOPE REPROCESSOR

BACKGROUND OF THE INVENTION

The present invention relates to the field of cleaning and disinfection or sterilization of devices with narrow lumens. It finds particular application in conjunction with cleaning and disinfecting flexible endoscopes, and will be described with particular reference thereto. It should be appreciated, however, that the invention is also applicable to the treatment of other lumened devices.

Fluid microbial decontamination systems are typically designed to cause microbes on the item to be removed or killed by a fluid antimicrobial agent. This is achieved in a variety of ways, including bath of antimicrobial liquid, spraying the item with antimicrobial liquid, surrounding the item with antimicrobial vapor, and the like. While such systems work well for killing microbes on the exterior surface of the items to be decontaminated, internal lumens can be problematic. To be a viable commercial product, a sterilization or disinfection apparatus must provide assured contact between the antimicrobial agent and the microbes. On items with elongated lumens, such as endoscopes, it is desirable that the antimicrobial fluid assuredly contact all surfaces within the lumen. Typically, this is achieved by pumping or drawing the antimicrobial fluid through the lumen. To accommodate differences between endoscopes, for example, in the size

BACKGROUND OF THE INVENTION

The present invention relates to the field of cleaning and disinfection or sterilization of devices with narrow lumens. It finds particular application in conjunction with cleaning and disinfecting flexible endoscopes, and will be described with particular reference thereto. It should be appreciated, however, that the invention is also applicable to the treatment of other lumened devices.

Fluid microbial decontamination systems are typically designed to cause microbes on the item to be removed or killed by a fluid antimicrobial agent. This is achieved in a variety of ways, including bath of antimicrobial liquid, spraying the item with antimicrobial liquid, surrounding the item with antimicrobial vapor, and the like. While such systems work well for killing microbes on the exterior surface of the items to be decontaminated, internal lumens can be problematic. To be a viable commercial product, a sterilization or disinfection apparatus must provide assured contact between the antimicrobial agent and the microbes. On items with elongated lumens, such as endoscopes, it is desirable that the antimicrobial fluid assuredly contact all surfaces within the lumen. Typically, this is achieved by pumping or drawing the antimicrobial fluid through the lumen. To accommodate differences between endoscopes, for example, in the size of the insertion tube or connector cord, the type and size of lumens, and the like, endoscope reprocessors are often limited to use with one or, at best, a family of similar endoscope types.

To force the cleaning fluid through the lumens of the endoscope, plugs and fittings are typically connected with the structures at the lumen ports. At the surfaces of interconnection, microbes can become trapped between the fittings or plugs and the structures at the lumen port. When there is a good frictional fit, the frictional fit protects these microbes from the antimicrobial agent. This creates the possibility that at the end of the cycle there may be active microbes on the surfaces adjacent the lumen ports destroying the assurance of disinfection or sterility.

One solution to the trapped microbe problem is to provide a pressure chamber, which is connected with the circulating fluid, for receiving an endoscope head. The endoscope insertion tube is conducted through a pipeline connected with an opening in the pressure chamber wall. However, due to variations in the diameter of the endoscope insertion tube, excessive leakage of fluid around the insertion tube, through the opening, can lead to pressure reductions in the chamber. The reduced pressure may then be insufficient to force the cleaning solution through lumens in the head.

The present invention provides a new and improved apparatus and method, which overcomes the above-referenced problems and others.

SUMMARY OF THE INVENTION

In accordance with one aspect of the present invention, a system for reprocessing a medical device having a tubular member with a lumen is provided. The system includes a container, which defines a pressure chamber into which a portion of the medical device is inserted. The container includes a first container portion, which defines a first portion of the pressure chamber and a first channel. A second container portion defines a second portion of the chamber and a second channel. The first and second channels together form an outlet from the pressure chamber when the container portions are in a closed position. The outlet receives the tubular member of the medical device therethrough. A flexing gasket assembly permits a restricted flow of reprocessing liquid through the pressure chamber outlet between the tubular member and the flexing gasket assembly when the tubular member is received therein. A pump supplies pressurized reprocessing liquid to the pressure chamber such that the reprocessing liquid flows through the lumen and between the tubular member and the flexing gasket.

In accordance with another aspect of the invention, a method for reprocessing an endoscope is provided. The method includes positioning the endoscope such that a head of the endoscope is received in a pressure chamber defined by first and second container portions and a tubular member of the endoscope extends through an outlet to the pressure chamber. A reprocessing liquid is flowed into the chamber and is flowed out of the chamber via a lumen in the tubular member and between the outlet and the tubular member. The method further includes restricting liquid flow between the outlet and the tubular member with a plurality of resiliently flexible fins.

In accordance with another aspect of the invention, a container for receiving an endoscope head is provided. The container includes a chamber, which receives the endoscope head. A tube extends from the chamber for receiving an insertion tube of the endoscope. An outlet from the chamber receives a connector cord. A plurality of fins is provided, each including a base portion selectively connected to the outlet and a rib, which extends from the base. The rib defines a slot for receiving the connector cord therethrough. The slots of the respective ribs decrease in size from a distal end to an outlet end of the outlet.

In accordance with another aspect of the present invention, a system for reprocessing a medical device is provided. The system includes a reprocessing chamber and a container received by the reprocessing chamber which defines an interior chamber for selectively receiving at least a portion of the medical device. A pump supplies a reprocessing liquid to the interior chamber to contact surfaces of the device. An indicator holder is carried by the container for selectively receiving an indicator. The indicator exhibits a detectable change in response to exposure to the reprocessing liquid.

One advantage of the present invention is that it enables interior and exterior surfaces of an endoscope to be cleaned and disinfected in a single reprocessor.

Another advantage of at least one embodiment of the present invention is that the reprocessor can accommodate different sized endoscopes.

Another advantage resides in controlled and assured flow, through lumens.

Yet another advantage of the present invention is that reprocessing fluid is allowed to leak controllably across all surfaces of the endoscope that engage the reprocessor.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

FIG. 10 is a schematic view of a light guide cord passing through an outlet;

FIG. 11 is a schematic view of a larger light guide cord passing through the outlet of FIG. 10;

DETAILED DESCRIPTION OF THE PREFERRED EMBODIMENTS

Figure 1:
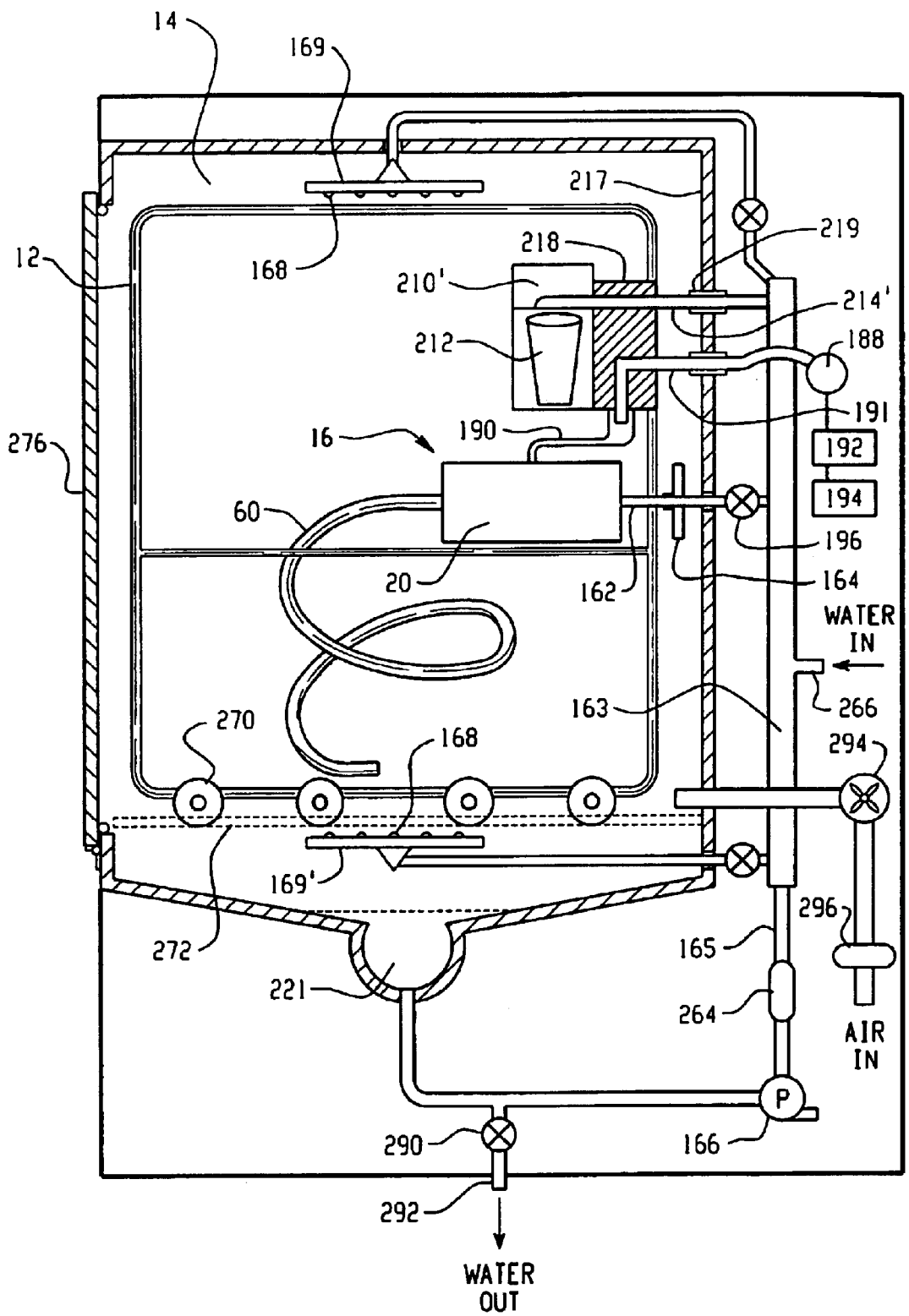
FIG. 1 is a side sectional view of an automated endoscope reprocessor according to the present invention.

With reference to FIG. 1, an automated endoscope reprocessor 10 is configured for rolling receipt of a wheeled cart or rack 12 in a washing/disinfecting chamber 14. The reprocessor chamber 14 is preferably about 10–15 liters in interior volume. The processor is sized to fit under counters or other work surfaces. However, higher installation locations and other size processors are also contemplated.

While the reprocessor 10 is described herein with particular reference to both cleaning and disinfecting steps (herein referred to generally as reprocessing), it is also contemplated that these steps are optionally combined, additional steps are employed, or that one or other of the steps is eliminated. Additionally, while disinfection, which refers to the destruction or inactivation of all harmful microorganisms, is generally desired, it is also contemplated that higher levels of antimicrobial treatment are achieved, such as sterilization (the destruction or inactivation of all microorganisms, whether harmful or not), or lower levels, such as sanitization. The various levels of decontamination can be achieved by adjusting the selected chemical agent, concentration of the chemical agent, cycle time, and the like.

Figure 2:
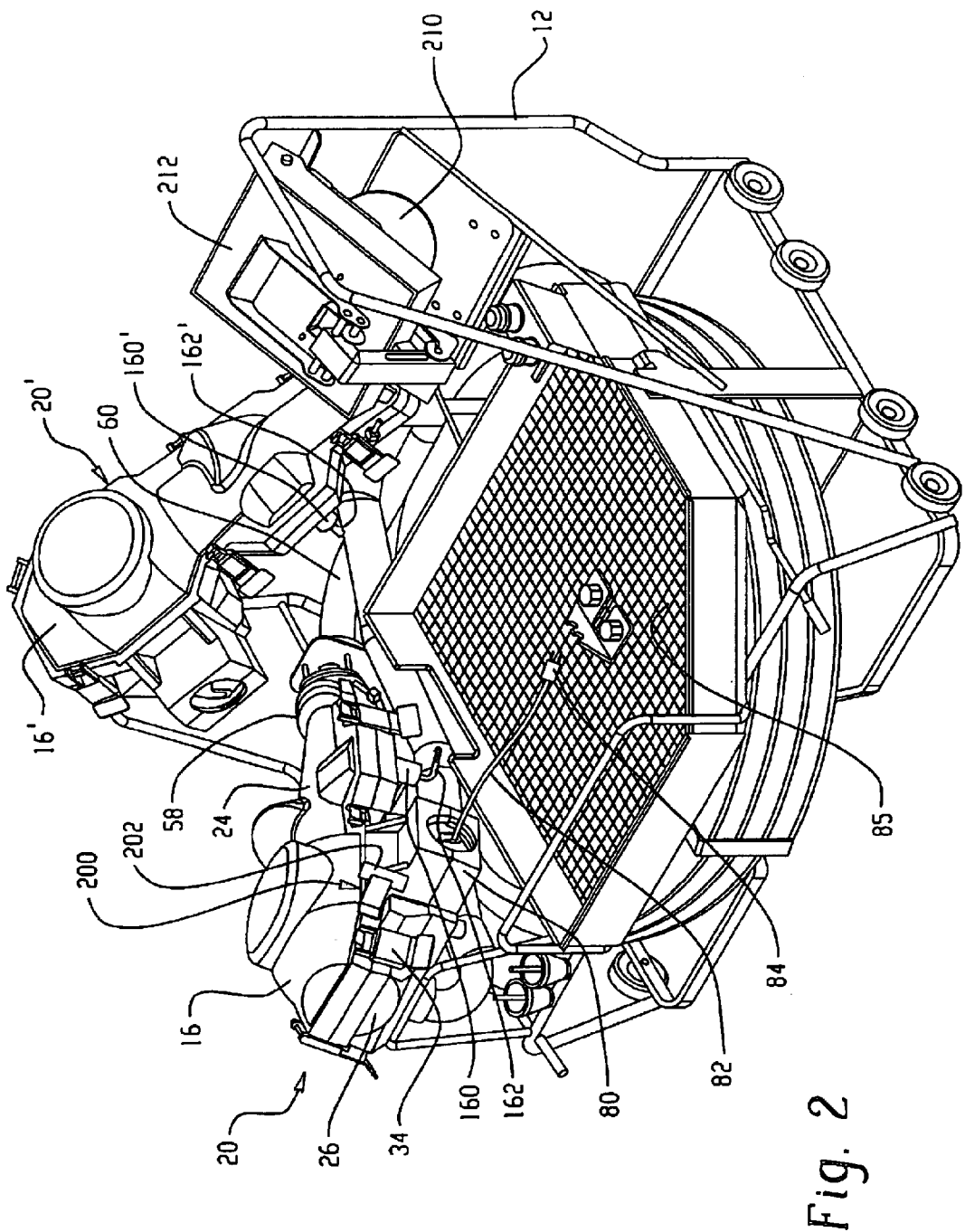
FIG. 2 is a perspective view of a rack of the endoscope reprocessor of FIG. 1 supporting two closed endoscope head containers.

With reference also to FIG. 2, the illustrated cart 12 is adapted to accommodate two endoscope head receiving containers 16, 16', generally positioned at right angles to one another, although it is contemplated that fewer or more containers may be accommodated. Additionally, while the reprocessor is particularly suited to reprocessing of endoscopes, the reprocessor is also suited to reprocessing a variety of other lumened devices. The term "endoscope," as used herein, is intended to encompass endoscopes, laparoscopes, bronchoscopes, colonoscopes, gastroscopes, duodenoscopes, and other, similar lumened devices.

Figure 3:
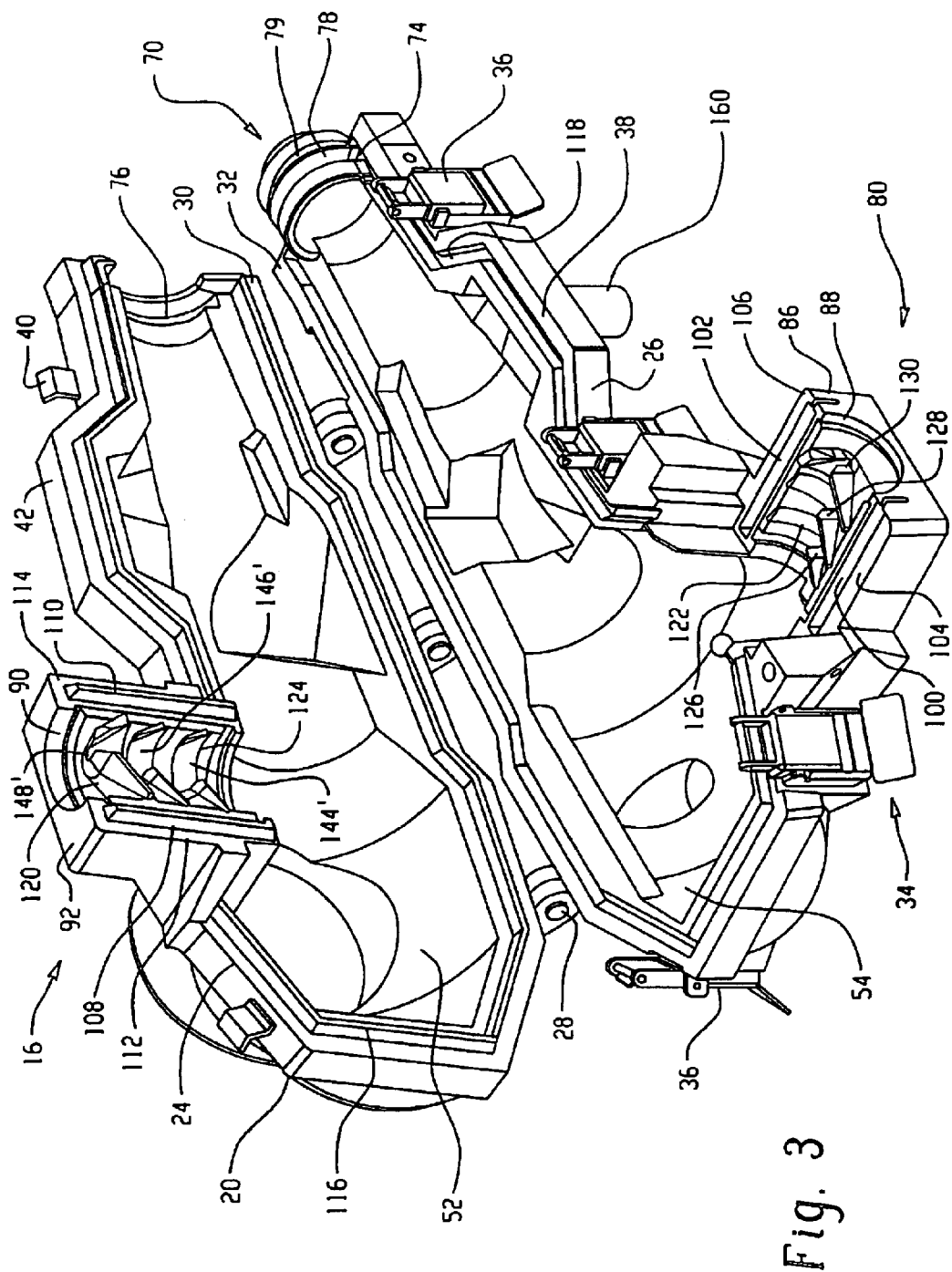
FIG. 3 is a perspective view of an open endoscope head container.
Figure 4:
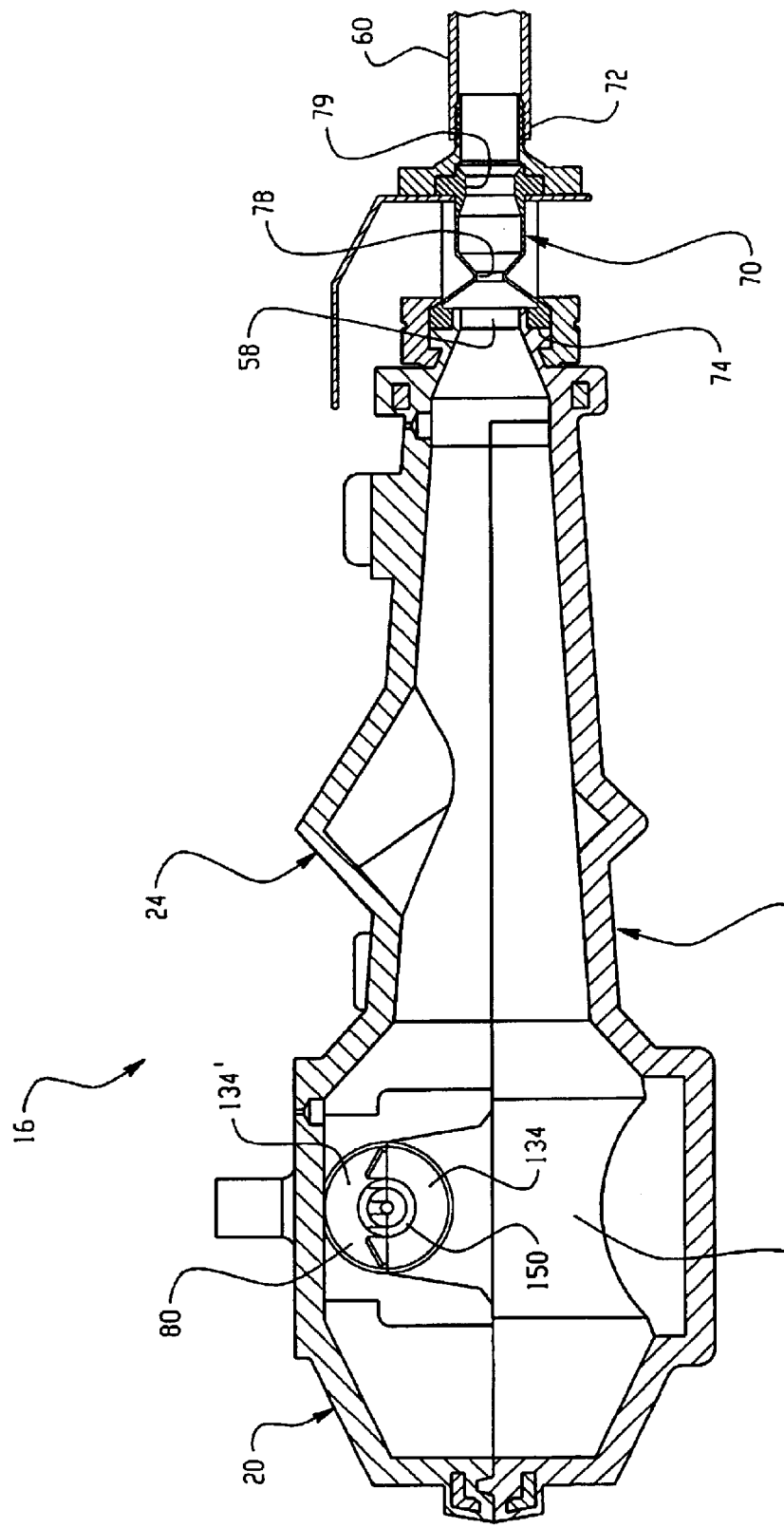
FIG. 4 is a side sectional view of the endoscope head container of FIG. 3.
Figure 5:
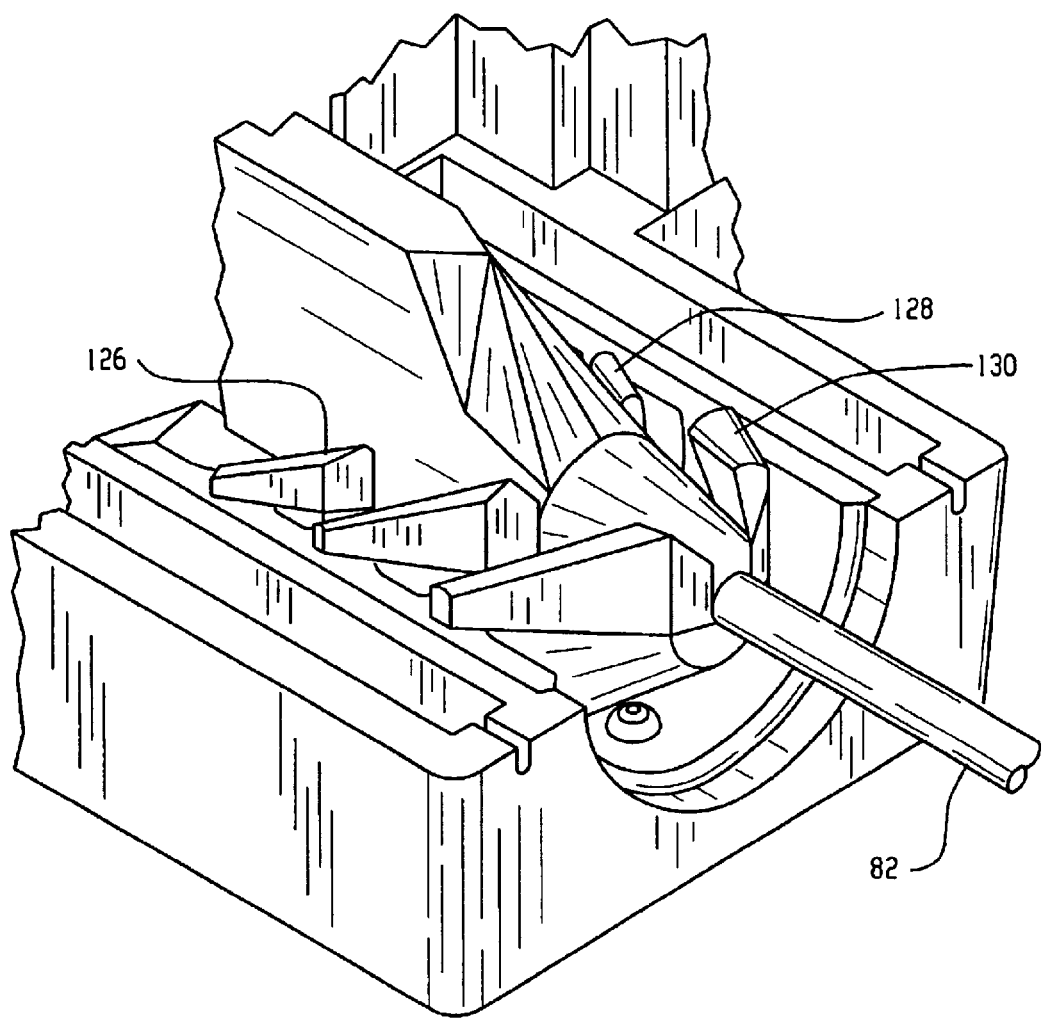
FIG. 5 is an enlarged perspective view of the lower portion of the endoscope head container of FIG. 3 showing an endoscope head in position.

As shown in FIGS. 2–6, each head receiving container 16, 16' includes a two-part clamshell housing 20, which is selectively openable to receive the head 22 of an endoscope. The head provides access to many of the internal lumens of the endoscope through openings or ports therein, as will be discussed in greater detail below. An upper portion 24 of the clamshell housing 20 is connected to a lower portion 26 of the housing by one or more pivoting members, such as hinges 28 mounted to adjacent sides 30 and 32 of the upper and lower portions, respectively (FIG. 3). A locking mechanism 34 holds the two container housing portions 24, 26 in leak-tight (or generally leak tight) engagement during a reprocessing cycle. An exemplary locking mechanism includes overcenter clamps comprising latches 36 (four are shown in FIGS. 2 and 4), spaced along one side 38 of one of the upper and lower portions, with corresponding catches 40 spaced along a corresponding side 42 of the other portion. Although the housing 20 is described with respect to two portions, it is contemplated that more than two portions are alternatively used.

With continued reference to FIG. 3, each of the container portions 24, 26 defines a basin 52, 54, which together form a cavity or pressure chamber 56 (FIG. 4) of an appropriate size and shape for receiving the endoscope head 22 when the portions are in a closed position. Endoscope heads vary in size and shape. The cavity is preferably shaped to accommodate at least one and preferably a plurality of different endoscope heads. The heads are held sufficiently loosely that fluid can contact all surfaces. Projections and recesses minimize direct contact area and prevent undue shifting.

Figure 7:
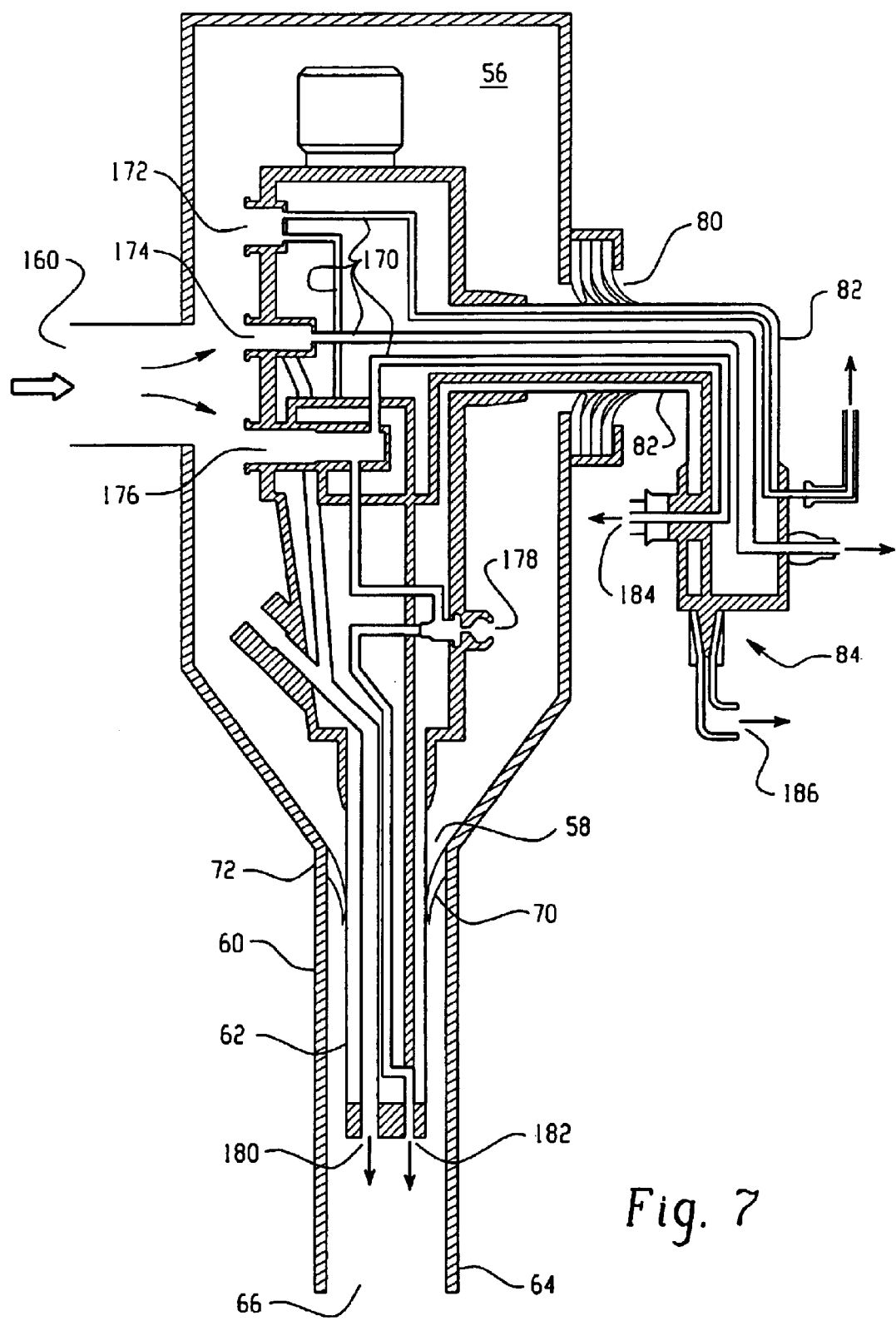
FIG. 7 is a schematic view showing fluid flow through lumens within an endoscope head in the endoscope head container.

As shown in FIGS. 2 and 7, an outlet 58 at one end of the pressure chamber 56 is connected with a long tube 60 of suitable dimensions to receive an insertion tube 62 of the endoscope. The tube 60 is preferably formed of a flexible material, such as polyethylene or fiber reinforced polyvinyl chloride. As shown in FIG. 1, the tube 60 is coiled in the reprocessor chamber 14 so that the insertion tube is not bent beyond the curvature which it can reasonably withstand. An end 64 of the tube distal from the housing 20 has an opening 66 such that fluid passes from the housing, through the tube, and around the endoscope insertion tube 62, before exiting the tube 60 at its open end (FIG. 7). The end of the tube 60 and optionally intermediate portions are clamped to rigid portions of the rack 12 to fix the position and shape the tube.

Since insertion tubes 62 are of different sizes and diameters, different insertion tubes offer different degrees of obstruction to fluid flow through the tube 60. To maintain a selected fluid pressure within the housing while allowing a steady, controlled flow through the tube 60, it is desirable to control the rate of fluid flow through the tube 60. In the preferred embodiment, this is achieved with a flexible restriction, such as a tapered, elastomeric gasket 70, best shown in FIGS. 3 and 4, which is preferably anchored in the clamshell housing at or adjacent an end 72 of the tube 60 proximal to the housing, or in the tube itself. As shown in FIGS. 3 and 4, the gasket 70 sits in a grooved U-shaped channel 74 at the end of the lower portion. When the container 16, 16' is closed a corresponding grooved U-shaped channel 76 in the upper portion is seated at an upper end of the gasket. The two grooved channels 74, 76, together define the chamber outlet 58. Alternatively, the outlet 58 may be defined entirely in one or other of the container housing portions 24, 26. The gasket expands to receive different diameter tubes. Alternatively, the gasket 70 may be positioned adjacent the distal end 64 or even in intermediate regions of the tube 60. Optionally, a plurality of interchangeable gaskets 70 is provided to accommodate a wider range of different diameter insertion tubes. The slope of the gasket taper, the diameter of the terminal opening, and the thickness and resiliency of the elastomeric material are selected to engage both a small diameter insertion tube and a large diameter insertion close enough to provide restricted flow between the gasket 70 and the endoscope tube 62 but not tight enough to strangle flow. For example, as shown in FIGS. 3 and 4, the gasket has two or more constrictions 78, 79.

Figure 6:
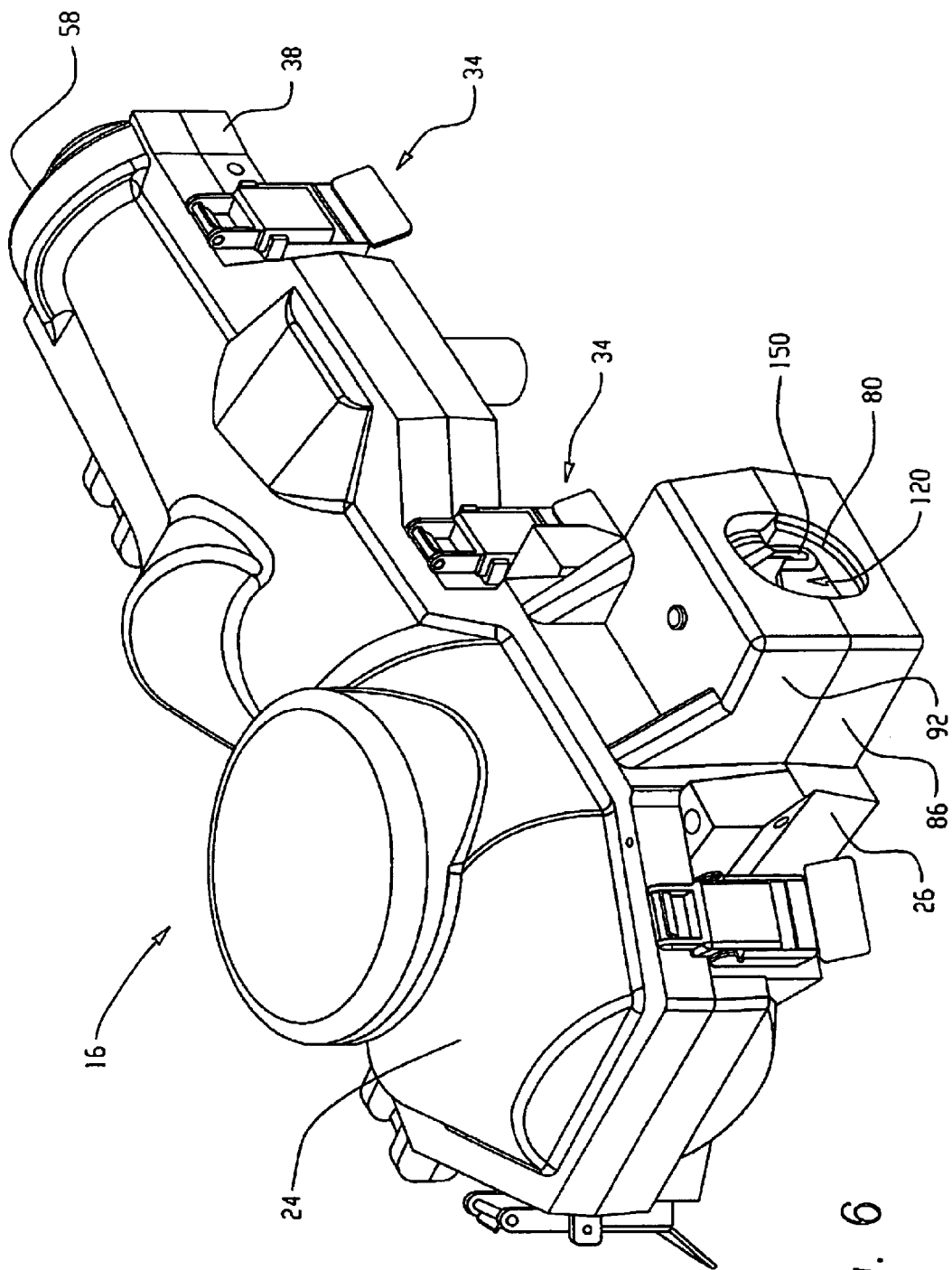
FIG. 6 is a perspective view of the endoscope head container of FIG. 3 in a closed position.

With reference to FIGS. 2–7, the housing includes an outlet 80 through which a flexible tubular member of the endoscope, such as a light guide connector cord 82 passes (FIG. 7). A light guide connector 84 and its associated cord 82 are then arranged on a horizontal mesh basket 85 of the cart 12 so that their exterior surfaces are cleaned and disinfected in the reprocessor (FIG. 2). The outlet 80 is formed in part by the upper portion and in part by the lower portion. As best shown in FIG. 3, a lower outlet member 86, which defines a U-shaped, preferably semicylindrical channel 88, extends from the basin 54 of the lower portion 26. A corresponding semicylindrical channel 90 is formed in an upper outlet member 92 extending from the upper portion 24. The semicylindrical channels 88, 90 mate with each other when the housing is closed, thereby defining the generally cylindrical outlet 80 (FIG. 6).

As best shown in FIG. 3, grooves 100, 102 formed in mating edges 104, 106 of one of the outlet members 86, 92 receive sealing members 108, 110 which protrude from corresponding mating edges 112, 114 of the other of the outlet members. When the overcenter clamps 34 are fastened, each sealing member 108, 110, is pressed into the corresponding groove, forming a longitudinal leak-tight joint along the outlet 80. A similar sealing member 116 runs around the basin 52 of the upper portion and is sealingly received in a corresponding groove 118 in the lower portion. Fluid exiting the housing is thus restricted to passing through the tube 60 or outlet 80.

Figure 8:
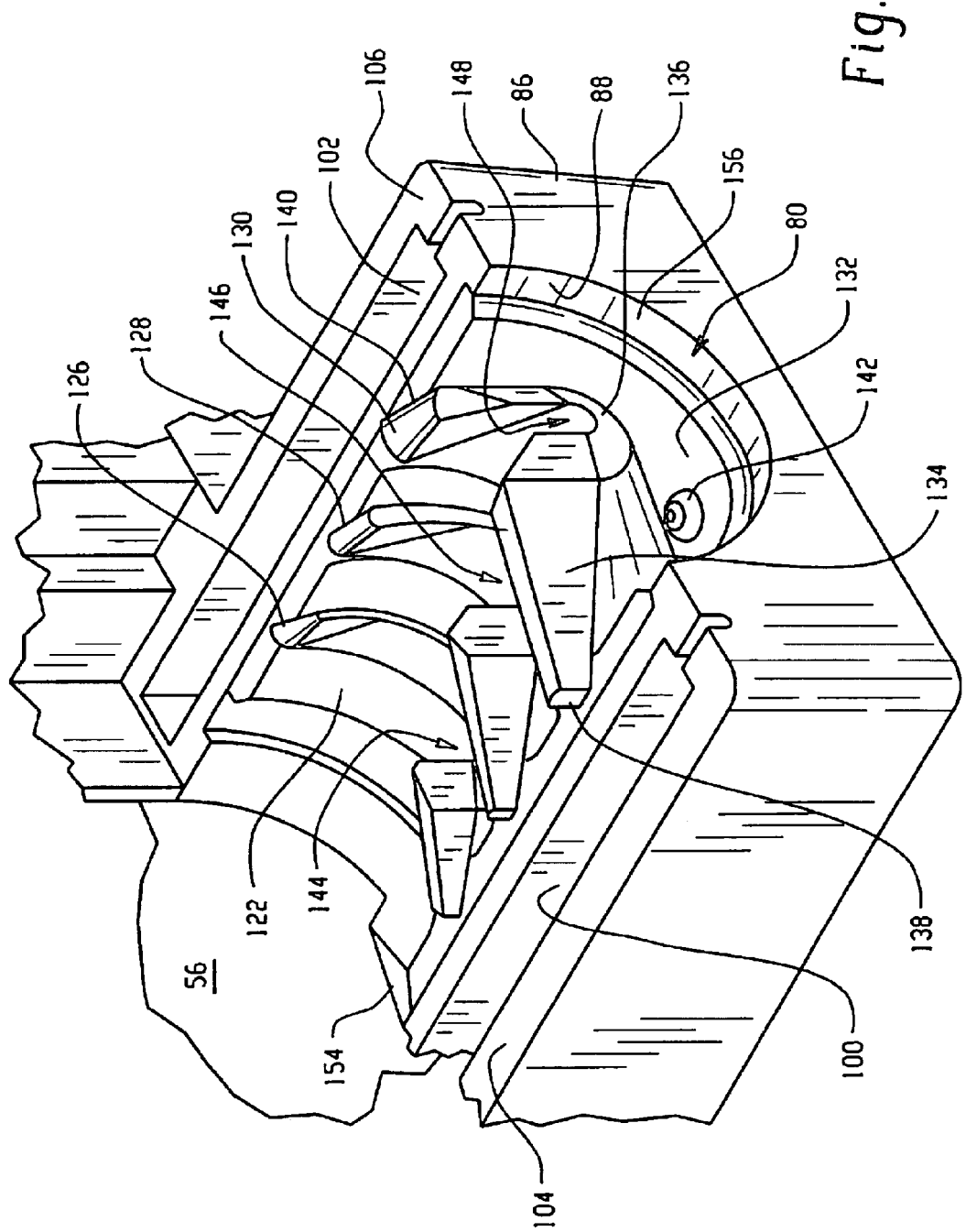
FIG. 8 is an enlarged perspective view of the outlet of FIG. 3.
Figure 9:
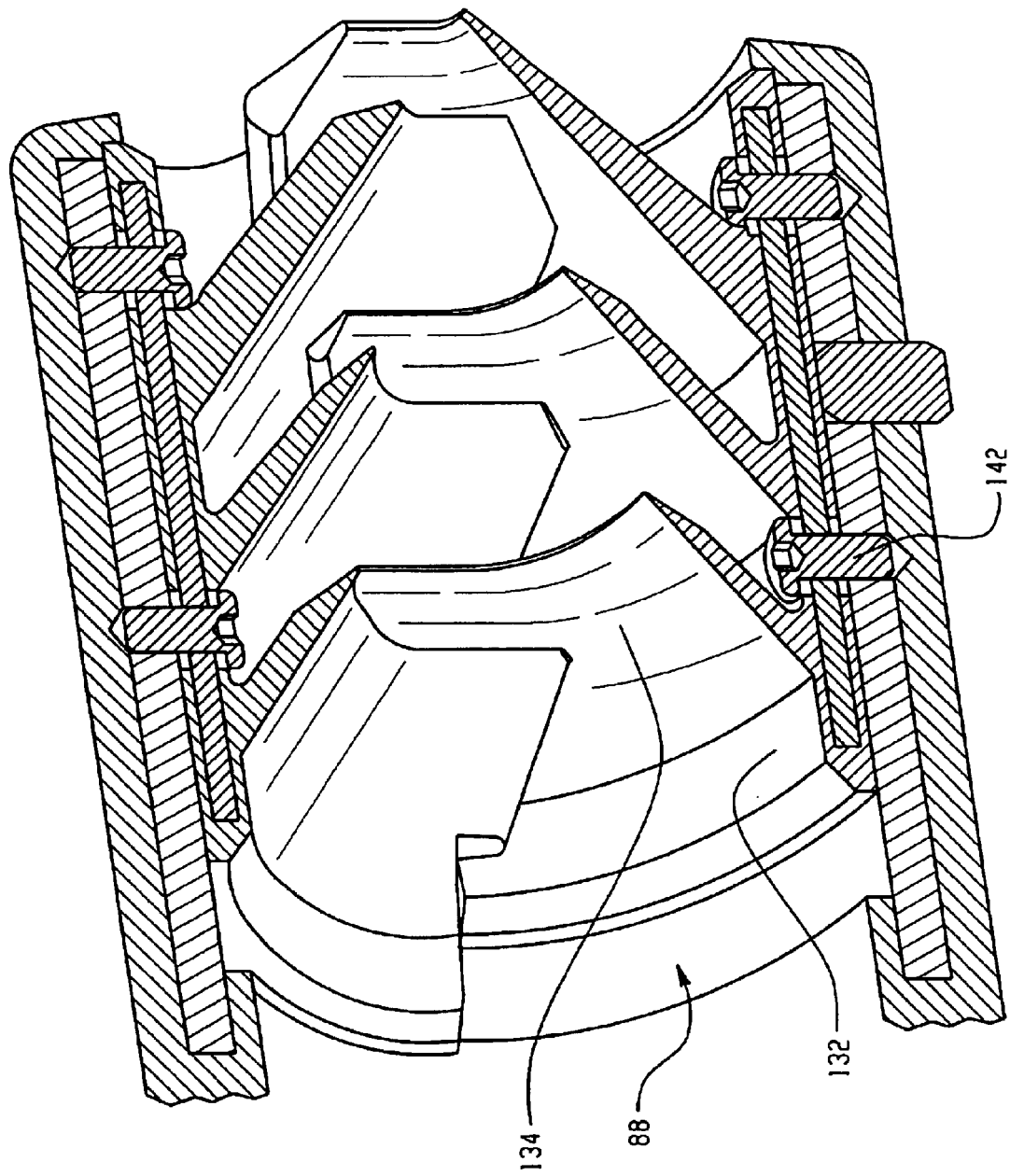
FIG. 9 is a perspective view, in partial section of the outlet of FIG. 8.

With reference also to FIG. 8, a multi-sized restrictor, such as a gasket assembly 120, is positioned within the outlet. The gasket assembly limits the flow of reprocessing liquid from the housing into the main reprocessor chamber 14. The gasket assembly is partly in the lower channel 88 and partly in the upper channel 90. Specifically, a first part 122 of the gasket assembly is seated in the channel 88 and a second part 124 is seated in the channel 90. In a preferred embodiment, and with reference to FIG. 8, each gasket part is formed from a plurality of closely adjacent or overlapping flexible U-shaped fins 126, 128, 130, (three are shown in FIGS. 2, 3, and 8), formed for example, from a flexible silicone material. Each fin includes a base portion 132, which is seated in contact with the channel wall, and a curved, U-shaped, tapered rib 134, which extends from the base portion into the channel 88, 90. The rib 134 is thus angled away from the channel wall 88, 90 such that it at least partially interrupts the flow of liquid from the chamber 56. The rib 134 of one fin may partially overlap the base portion 132 of the successive downstream fin. As shown in FIG. 9, the base portions 132 and ribs 134 are preferably formed together as a single component 122, 124, i.e., all of the base portions are joined together, although it is also contemplated that each of the fins 126, 128, 130 may be separately formed and individually replaceable.

The ribs 134 are curved with a midpoint 136 of each rib being downstream of edges 138, 140 of the rib. The integral base comprising base portions 132 is preferably attached to the respective channel 88, 90 with screws 142, bolts, or other suitable fixing members so that the respective parts 122, 124 of the gasket assembly can be removed and/or replaced as will be discussed in greater detail below. Alternatively, the fins are welded, adhesively joined, or otherwise connected to the channel 88, 90 or to each other to form the respective gasket part 122, 124.

A U-shaped slot 144, 146, 148, is formed in each of the ribs 134 at around the midpoint, the slots being longitudinally aligned along the outlet 80. The ribs 134 of the fins of one channel 88 overlap, contact, or otherwise interengage the ribs of their corresponding fins on the other channel 90 such that pairs of slots 144, 144', 146, 146', and 148, 148', form a row of generally circular openings 150 (FIGS. 4 and 6). Preferably, the slots, and hence the circular openings 150 diminish in size from a proximal end 154 to a distal end 156 of the outlet 80, as shown in FIG. 8. This allows different sized light guide cords 82 to be accommodated while maintaining pressure within the housing 20 within preselected tolerances. The relatively small diameter light guide connector cord 82 exemplified in FIG. 10, engages only the outer fins 130, 130', while a larger diameter light guide connector cord 82' exemplified in FIG. 11, engages all or at least several of the fins 126, 128, 130. The fins shown in FIGS. 10 and 11 are illustrated as simple flaps for convenience, and an additional, fourth fin 158, is also shown. As the fins 126, 128, 130, 158 are resiliently flexible, the ribs 134 are splayed outward around the openings 150 allowing the light guide connector cord 82, 82' to pass through. In each case, the pressure within the housing 20 is readily maintained at a pressure of at least about 17 kPa, more preferably, around 70 kPa. A flow of reprocessing liquid leaks out of the housing through the fin openings, ensuring that all exterior surfaces are contacted with the cleaning and disinfectant liquids (referred to generally herein as reprocessing liquids).

Optionally, one or more, or the entire set of fins 126, 128, 130 is replaceable. For example, one set of fins is used for medium to large connector cords, while for small cords, e.g., bronchoscopes, one or more of the fins is replaced by a fin or fins having smaller slots 144, 146, 148. This is readily achieved by unscrewing one or more of the fin screws 142 and attaching appropriate replacement fins. Optionally, other fastening systems are employed which utilize other external fasteners or the resiliency of the gasket part 122, 124 to snap fit or friction hold it to the respective channel 88, 90.

As shown in FIGS. 1, 3, and 7, reprocessing liquids enter the housing 20 through an inlet 160 formed in one of the upper and lower portions 24, 26 of the housing 20. A hose 162 is selectively connected between the inlet 160 and a manifold 163. The manifold 163 interconnects with a fluid outlet 164 in the back of the chamber 14, preferably with a friction fitting. The outlet 164 is connected to a fluid distribution system 165 of the reprocessor. Cleaning/disinfectant liquid is pumped under pressure through fluid distribution system 165 to the hose 162 by a pump 166. The same pump 166 optionally also supplies reprocessing liquids under pressure via the fluid distribution system 165 to nozzles 168 disposed within the washing chamber 14 (FIG. 1). The nozzles 168 are preferably in the form of holes formed, for example, in upper and lower rotating spray bars or heads 169, 169'. The cleaning/disinfectant liquids are supplied to the housing 20 at a sufficient pressure to maintain a pressure in the housing which exceeds the ambient pressure within the reprocessor chamber 14. The pressure within the housing 20 is below that which could cause damage to delicate components of the endoscope but is sufficient to force the liquids through the lumens of the endoscope which are to be cleaned. An over-pressure within the housing 20 of about 70 kPa, relative to the pressure within the main reprocessor chamber 14, is preferred for most types of endoscope, although for some endoscopes having very narrow lumens, higher pressures may be desirable.

As illustrated in FIG. 7, a portion of the reprocessing liquid entering the housing 20 flows around the endoscope head 22, cleaning/disinfecting the exterior thereof. Some of this liquid exits the housing 20 through the tube 60 and some exits through the outlet 80. A portion of the liquid entering the housing enters the lumens 170 of the endoscope via inlet ports 172, 174, 176, etc. in the head 22 and passes through the lumens to their respective outlet ports 180, 182, 184, 186, etc., such as at the end of the insertion tube 62 or in the light guide connector 84. Optionally, one or more of the endoscope inlet or outlet ports is fitted with an adapter (not shown) to mechanically actuate a valve, which would otherwise prevent circulation of fluid. Alternatively, one or more ports is blocked or restricted with a plug (not shown), which blocks or restricts the flow of liquid into or out of the respective port. This ensures liquid flow in all the lumens to be cleaned/disinfected. As another option, additional inlet ports, jets, or baffles are arranged to direct extra fluid or raise the pressure adjacent hard to penetrate lumen channels.

Figure 14:
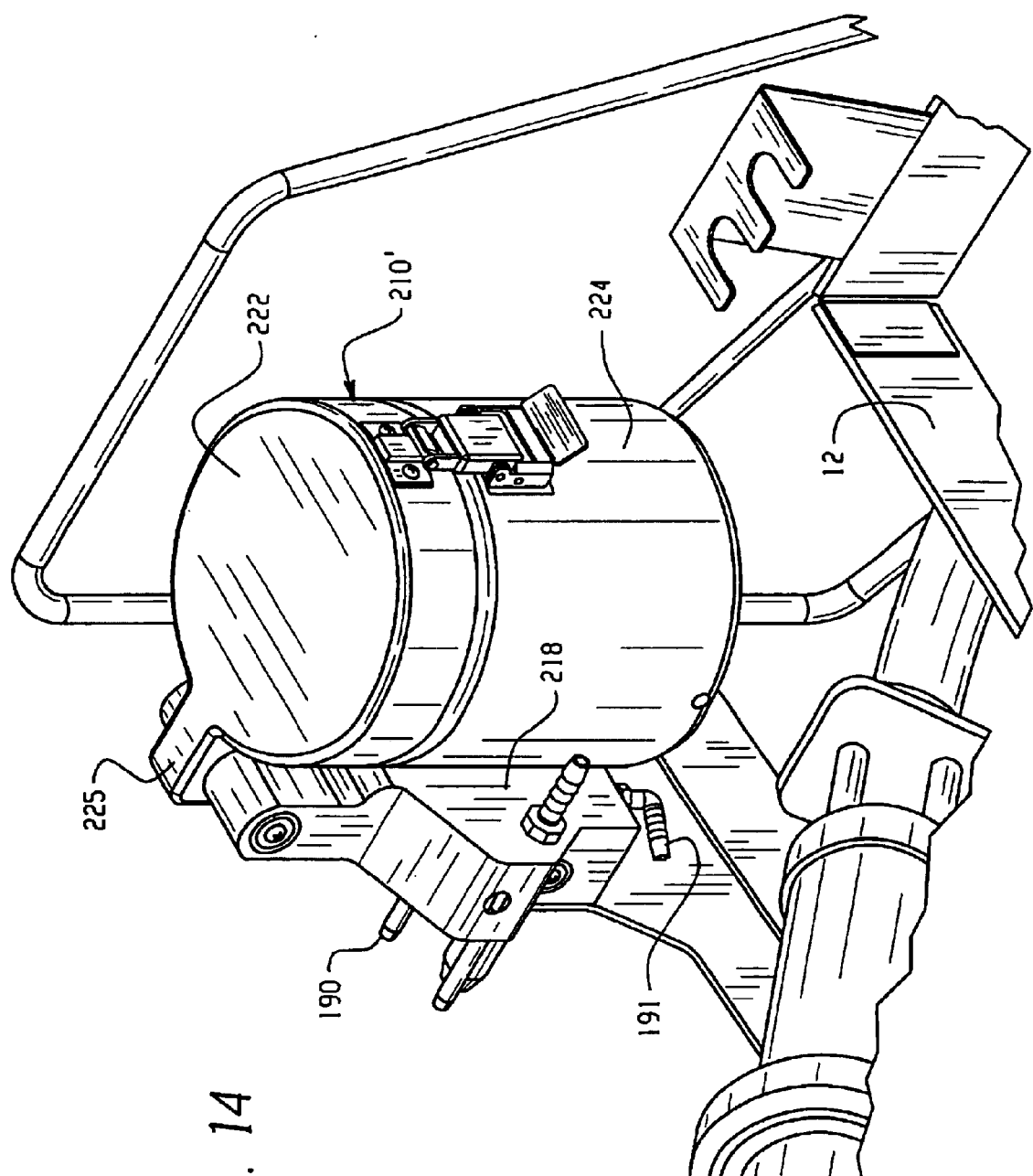
FIG. 14 is a perspective view of an alternative embodiment of a cartridge holder in accordance with the present invention.
Figure 16:
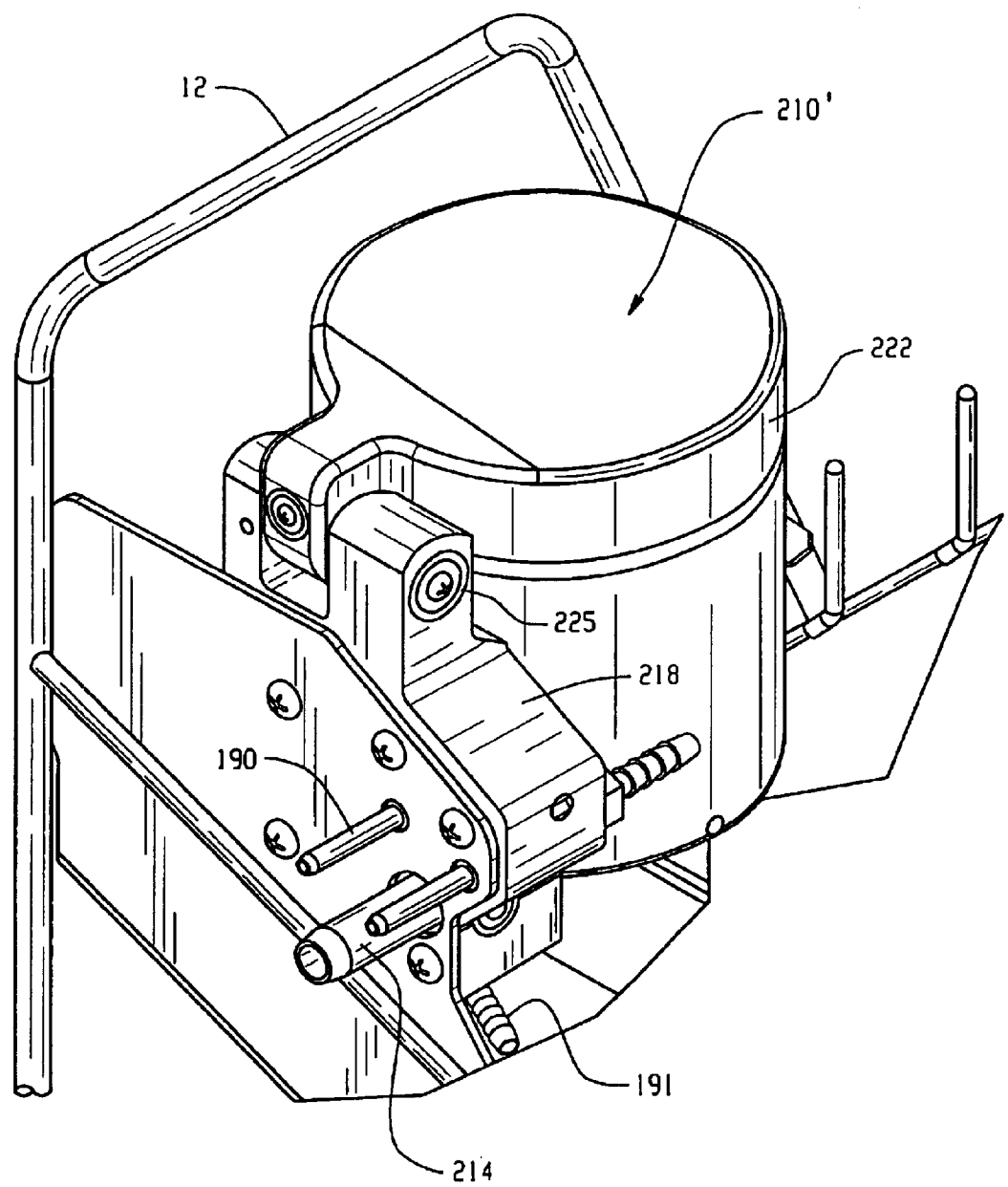
FIG. 16 is a rear perspective view of the cartridge holder of FIG. 14.

To ensure that the pressure within the housing 20 is maintained within a preselected range throughout a decontamination cycle (i.e., high enough to ensure lumen flow but not so high as to cause damage), a pressure relief valve or a pressure sensor, such as a pressure transducer 188, is mounted so as to detect pressure within the housing 20. For example, as shown in FIGS. 1, 14, and 16, the pressure transducer 188 is mounted outside the reprocessor chamber 14 and detects pressure within the housing 20 via interconnecting tubes 190, 191. Interconnecting tube 191 is automatically connected with a chamber wall connector (not shown) when the rack 12 is pushed fully back into the reprocessor chamber 14. The pressure transducer is connected with a control system 192, which monitors the detected pressures and accesses an algorithm, look-up table, or the like. If the pressure detected falls below a minimum preselected pressure or rises above a maximum preselected pressure, the control system 192 makes a response. The response may be to actuate an alarm 194, such as a siren or flashing light, which indicates to an operator that the pressure is outside the desired range. Or, the control system may abort the cycle. In yet another embodiment, the control system 192 controls the pump 166 to increase or decrease the pressure of liquid until the pressure within the housing 20 is in the preselected range. In yet another embodiment, the control system 192 controls a controllable restrictor 196 in the inlet hose, such as a solenoid valve, to limit or increase the volume of liquid entering the housing in accordance with the detected pressure.

Figure 12:
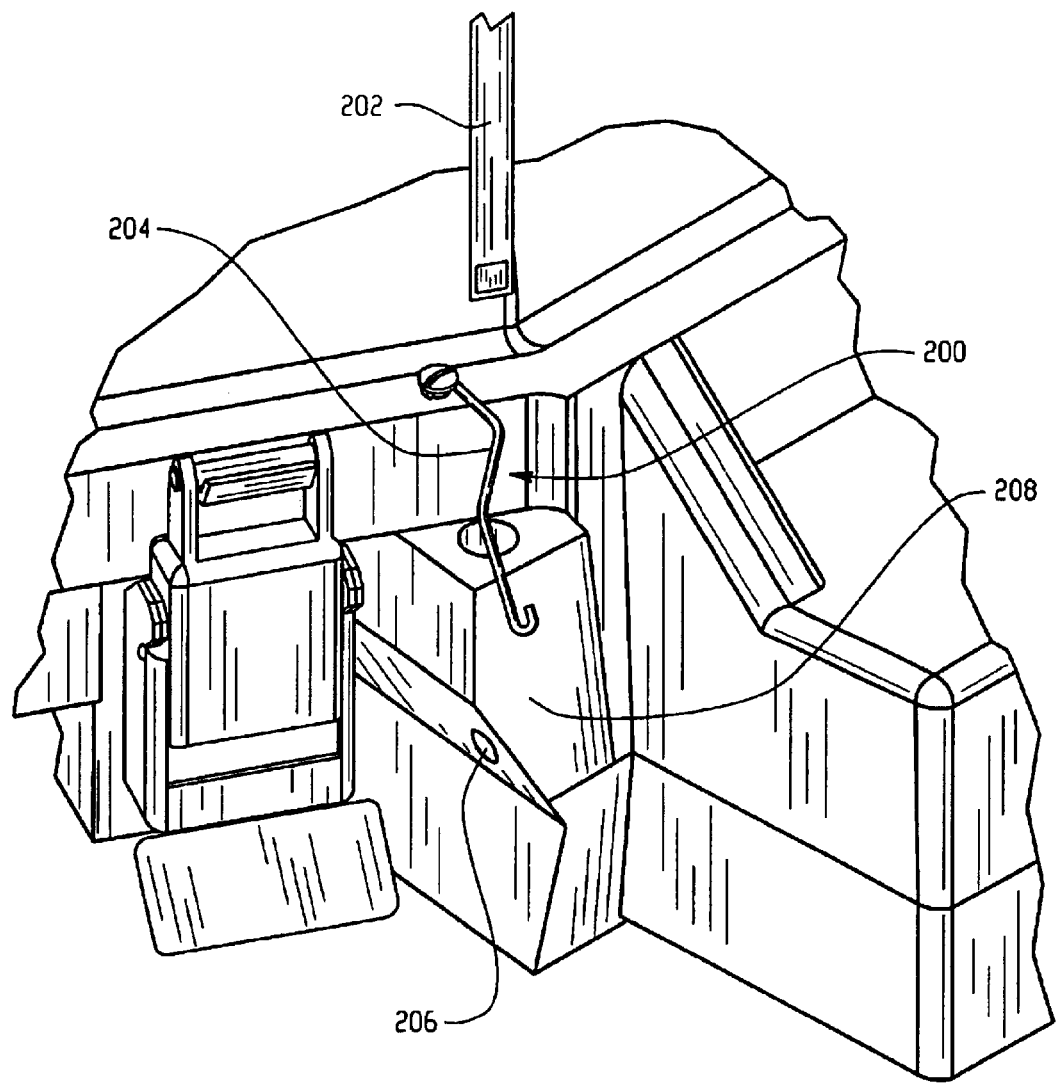
FIG. 12 is an enlarged perspective view of the endoscope head container of FIG. 3, showing an indicator strip and strip holder.
Figure 13:
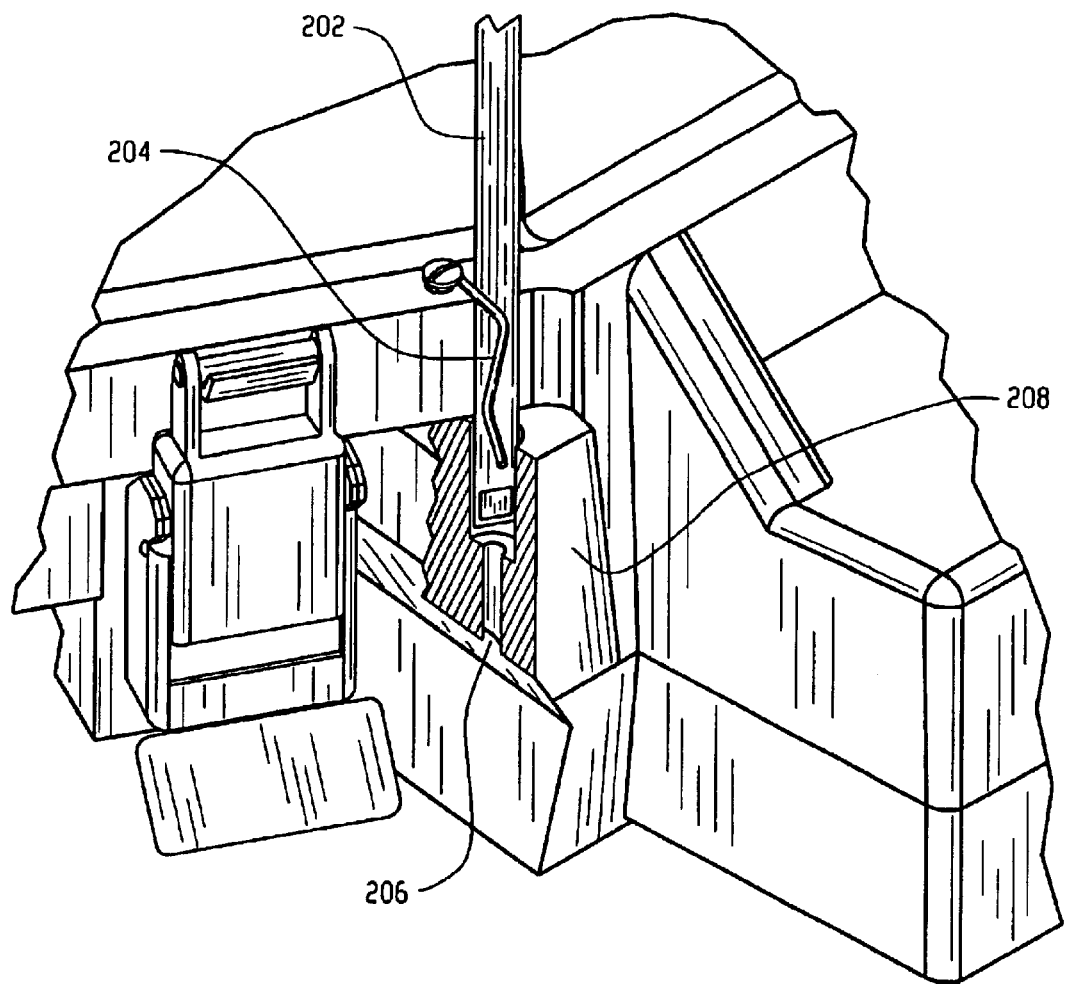
FIG. 13 is a perspective view in partial section of the strip holder of FIG. 12.

Optionally, an indicator holder 200 is mounted to the housing 20 (FIGS. 12 and 13). This ensures that the holder 200 is positioned within the reprocessor every time the head container 16, 16' is used. The holder 200 receives an indicator 202, such as a biological or chemical indicator, which is sensitive to one or more of the chemicals used in cleaning or disinfecting of the endoscope. For example, the indicator may include a strip impregnated with a chemical which changes color, or exhibits another physically or chemically detectable change, in response to being exposed to a concentration of the chemical for a period of time judged to be sufficient to effect cleaning or disinfection of the endoscope and/or other items within the reprocessor.

In the embodiment of FIGS. 12 and 13, for example, the holder includes a clip 204, which is mounted by a screw or other fastening device to the outside of the housing and grips one end of the strip. To provide a challenge to the flow of reprocessing liquid, the impregnated end of the strip is positioned partway along a bore 206, which narrows at its lower, counter-bored end. The bore is formed in a block 208 mounted to the outside of the housing 20. Solution flows through the bore 206 and contacts the chemical or biological indicator material at the end of the strip. The bore protects the indicator from damage by the powerful spray jets from the spray arms, which could otherwise remove the indicator reagents from the strip and lead to inaccurate results. At the same time the strip is exposed to the humid conditions within the chamber and is contacted by droplets of the reprocessing solution which pass through the bore.

Figure 19:
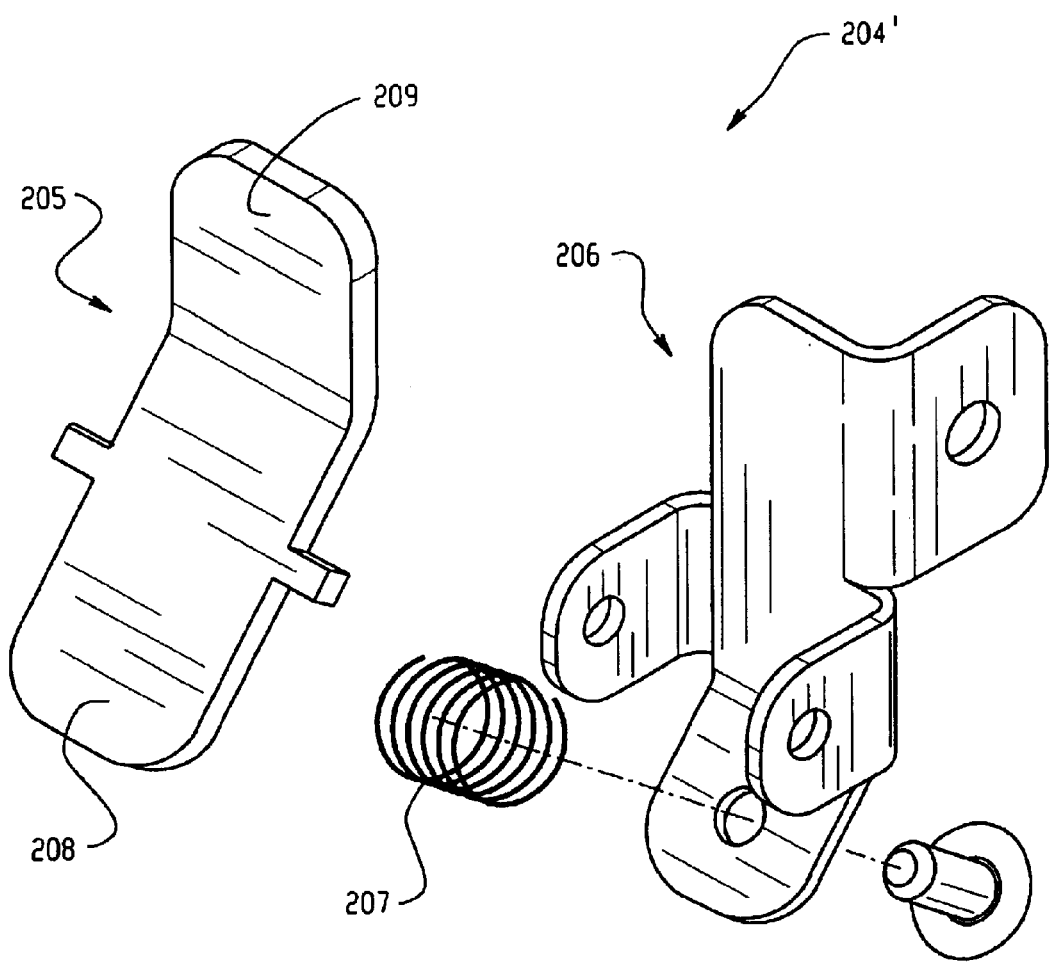
FIG. 19 is a perspective view of an alternative embodiment of the indicator clip of FIG. 13.

FIG. 19 shows an alternative embodiment of a clip 204'. The clip 204' includes a spring biased retaining member 205, which is pivotally attached to an attachment member 206 by pivot arms. The attachment member is attached to the housing by screws (not shown), an adhesive, or other suitable fixing members. A spring 207 biases a lower portion 208 of the attachment member outwardly, so that an upper portion 209 of the retaining member into clamping engagement with the attachment member to grip a portion of the indicator strip 202 therebetween.

The head container 16, 16' is preferably formed from a temperature resistant plastic or stainless steel, with the seals and gaskets being formed from alkali and acid resistant materials.

Figure 17:
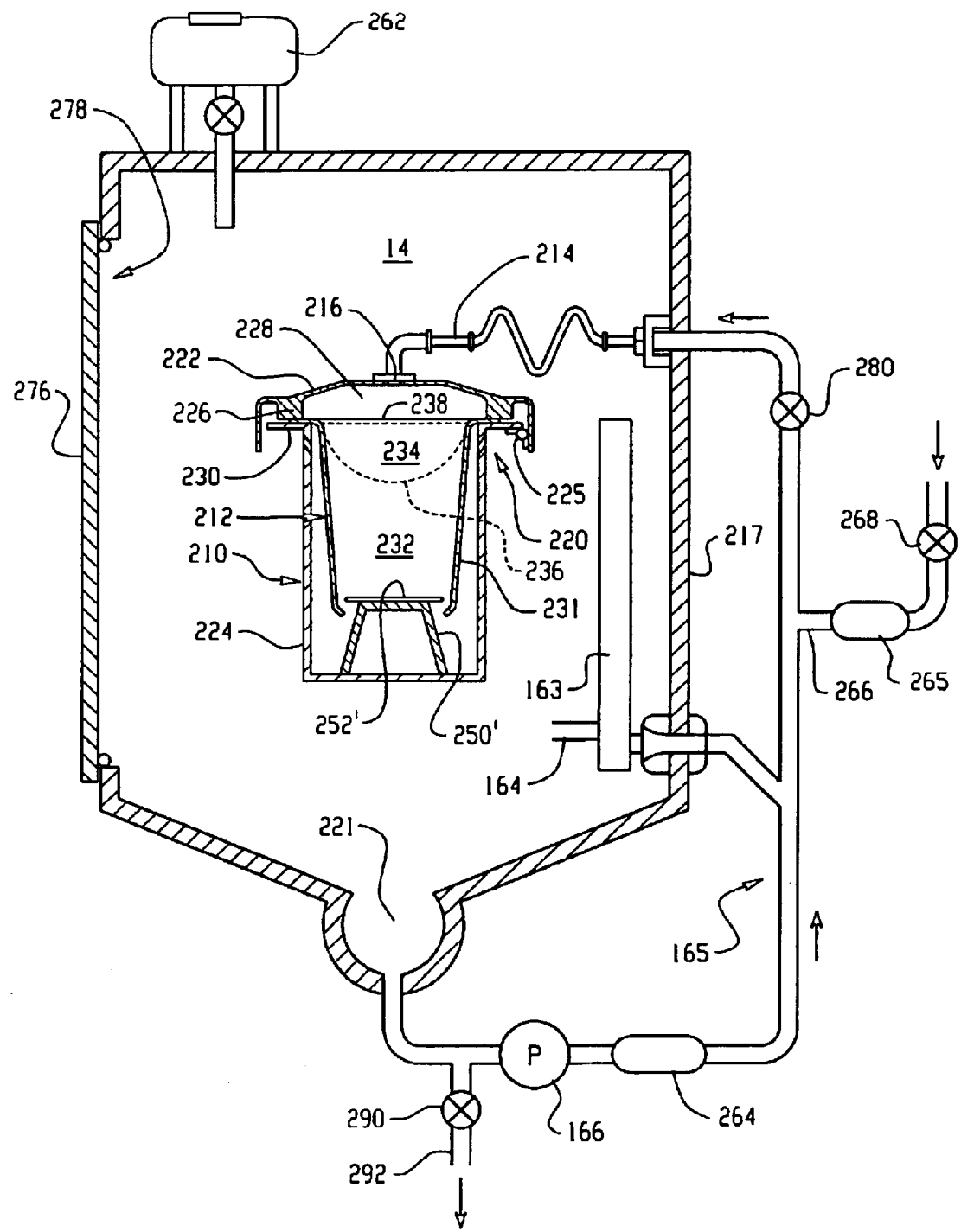
FIG. 17 is a schematic view of the reprocessor of FIG. 1 with a cartridge holder holding an opened cartridge.
Figure 18:
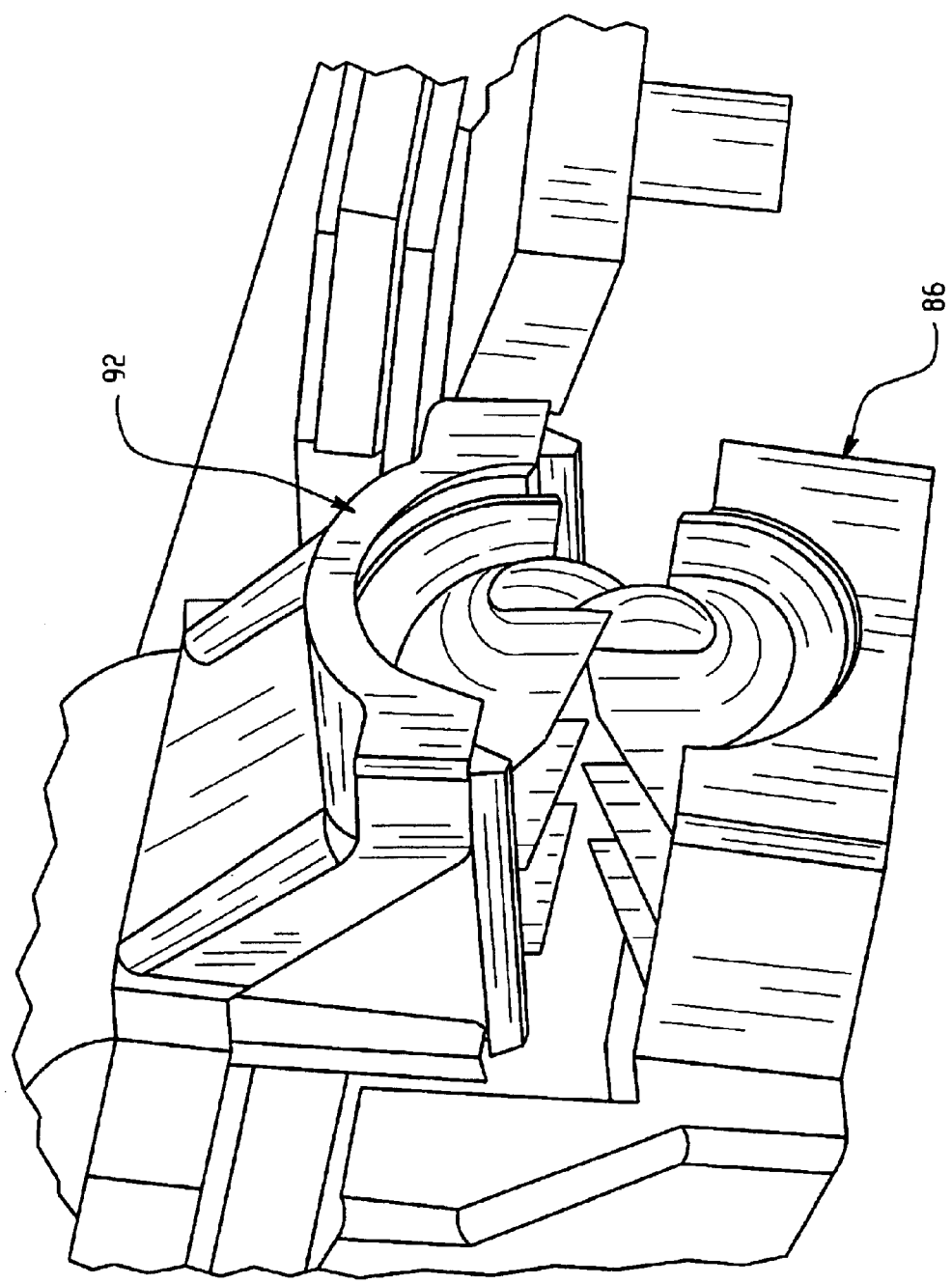
FIG. 18 is a perspective view of the outlet of FIG. 3 in a partially closed position.

With reference now to FIGS. 1 and 2 and 14–17, a cup or cartridge holder 210 is mounted in the reprocessor chamber 14, and is preferably supported on the cart 12. FIG. 2 shows a first embodiment of the cartridge holder. The cartridge holder 210' of FIGS. 14–17 is shaped somewhat differently. The holder 210, 210' receives a cartridge or cup 212 holding a predetermined, reproducible quantity of a concentrated source of reprocessing solution. In one embodiment, the source includes a cleaner concentrate and/or disinfectant concentrate. In the embodiment of FIG. 17, an extensible fluid inlet line 214 is fluidly connected between an inlet 216 to the holder and through a wall 217 of the chamber to the pump 166. In the embodiment of FIGS. 1, 14–16, a fluid inlet line 214' mounted to a rear wall 218 of the cartridge holder 210' couples with a connector 219 on the rear wall 217 of the reprocessing chamber 14 when the rack is pushed back fully into the reprocessing chamber. In this embodiment, the rear wall 218 of the holder 210' acts as a manifold for providing both the pressure testing connections (via interconnecting tubes 190, 191 and the water connections for the reprocessing chamber 14.

At least a portion of the water entering the reprocessor is thus passed through the cartridge 212 and mixes with the cleaner/disinfectant concentrate or reagents for forming a cleaner/disinfectant solution to form a cleaning/disinfectant solution. The solution flows out of the cartridge holder 210, 210' via one or more outlets 220 into the reprocessing chamber 14 and collects in a sump 221 at the base of the reprocessing chamber. The pump 166 recirculates the solution through the nozzles 168, the head containers 16, 16', and cup holder 210, 210', as discussed above.

Figure 15:
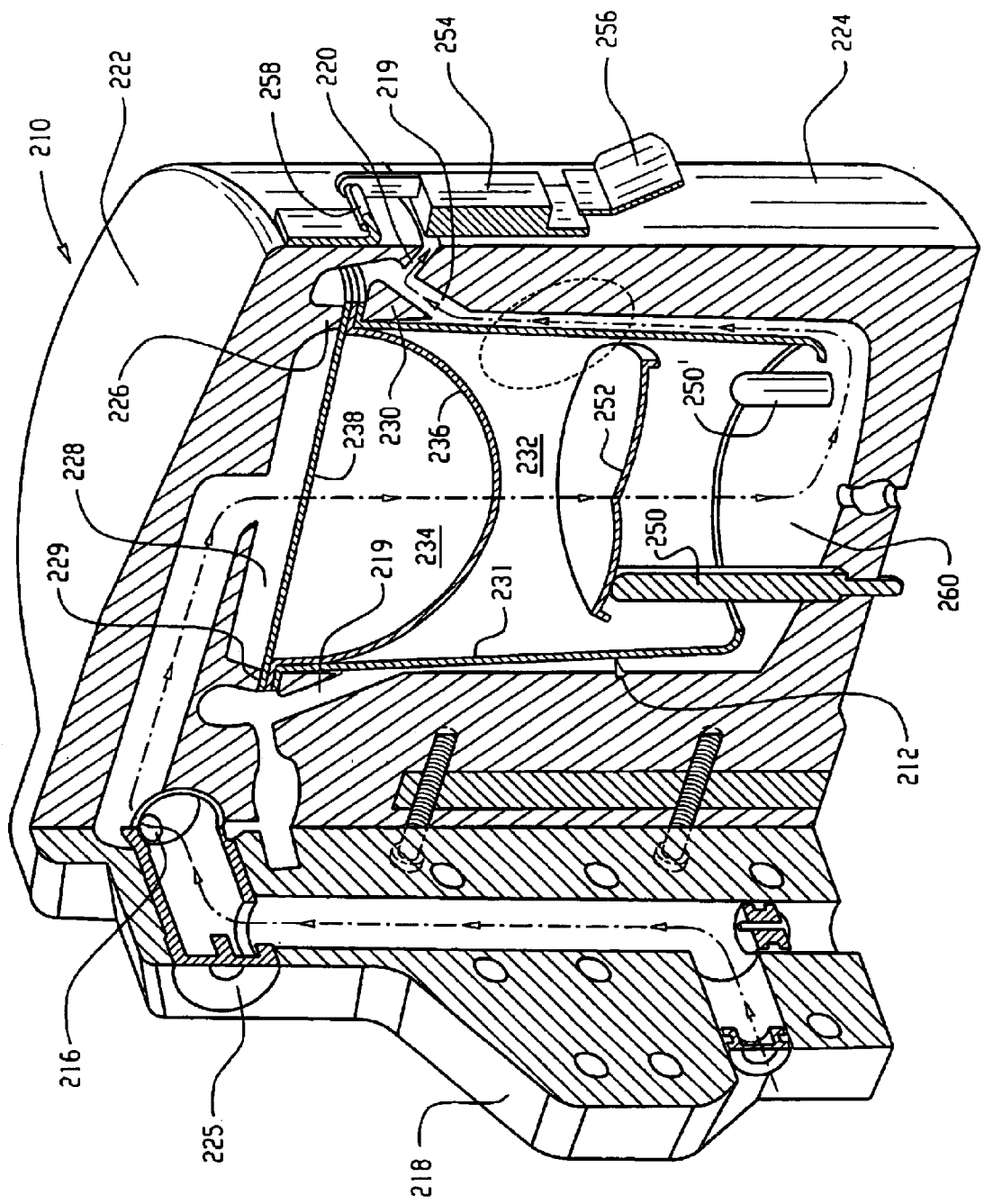
FIG. 15 is a perspective view, in partial section, of the cartridge holder of FIG. 14 in a closed position.

As shown in FIGS. 14–16, a preferred embodiment of the holder 210' includes a lid 222, which is pivotally connected to a base portion 224 by a hinge 225 or other suitable pivoting member, which is formed, in part, by the rear wall 218 of the holder. The holder inlet 216 is preferably formed in the lid 222, as shown in FIG. 15, although it is also contemplated that the inlet be formed in the base 224. The holder outlets 220 are in the base portion. An annular rim 226 projects from the lid 222 around an upper opening 228 of the base portion. An annular peripheral edge or flange 229 of the cup 212 is clamped between the rim 226 and an adjacent annular rim 230 of the base when the lid 222 is closed.

In a preferred embodiment, the cartridge 212 includes an outer cup portion 231, formed from a relatively rigid material, which defines a first interior compartment 232. A second interior compartment 234 is defined in an inner cup portion 236, which, in the preferred embodiment, is formed from a porous material, which is permeable to water and circulating cleaning/disinfectant solution. A porous lid or top cover 238 is sealed around its periphery to flanges of the inner and outer cup portions to create the flange 229 and the two compartments 232, 234.

The first compartment 232 contains a measured dose of a first treatment material, and the second compartment holds a measured dose of a second treatment material. Where the inner cup portion is porous, both treatment materials are preferably in solid form, for example, powders or other finely divided solid which readily disperse and dissolve in the water. For example, the first and second treatment materials are reagents which react in water to form a disinfectant solution. The disinfectant solution includes an oxidant, preferably a peracid, such as peracetic acid. For example, the first compartment may hold a peroxy donor, such as a perborate, e.g., sodium metaborate, and the second compartment, an acetyl donor, such as acetyl salicylic acid. These react in water to form the oxidant, peracetic acid in the preferred embodiment. One or other of the compartments may additionally contain other additives. For example, surfactants are included to increase removal of soil and improve penetration of the disinfectant solution into cracks and crevices, sequestering agents are added to combat water hardness, corrosion inhibitors reduce corrosion of the endoscope and reprocessor components by the disinfectant solution, and buffering agents buffer the disinfectant solution to a suitable pH for optimal disinfection.

In other embodiments, the cartridge 212 holds a liquid or solid disinfectant concentrate, a liquid or solid cleaning concentrate, both cleaning and disinfectant concentrates, or a combination cleaning/disinfectant concentrate.

The holder 210, 210' optionally includes an opening mechanism 250, which opens the cartridge to release the disinfectant solution. In the preferred embodiment, the opening mechanism includes one or more projections 250, 250' extending from a lower end of the holder base 224. In one embodiment, a pair of projections 250, 250' dislodge and push up a snap fit, removable base 252 of the cartridge outer cup portion 231 as the holder lid 222 is fastened down, as illustrated in FIG. 15. It is also contemplated that the opening mechanism may perforate or cut the cup 212.

The lid 222 is held in a closed position by an overcenter clamp 254, which clamps the lid 222 in position over the base 224 (FIG. 15). For example, a latch 256 is attached to the base 224 and engages a catch 258 on the lid (FIG. 15).

Water thus flows through the porous top 238 of the cartridge and mixes with the second reagent in the upper compartment 234. The water and dissolved second reagent passes through the porous second cup portion 236 and enters the lower compartment 232, where the first reagent dissolves and reacts with the dissolved second reagent to form the disinfectant solution. The disinfectant solution flows out of the cartridge via an opening 260 in the cartridge created by removal or otherwise opening of the base 252.

Alternatively, a ram (not shown) is selectively actuated to drive a piercing member through the cartridge base, and optionally also through one or more additional bases to one or more additional compartments in the cartridge. In one embodiment, the ram selectively releases a cleaner concentrate (which may be liquid or solid), which mixes with water to form a cleaning solution, and, subsequently, releases a disinfectant concentrate (which may be liquid or solid) or reagents, as discussed above, which react in water to form the disinfectant solution. The cleaner concentrate is preferably a liquid detergent and/or enzymatic cleaner. The cleaner concentrate optionally also includes additional additives, such as surfactants, buffering agents, chelating agents, corrosion inhibitors, and the like. The detergent helps to remove dirt from the items in the chamber which could otherwise limit the penetration and effectiveness of the disinfectant solution.

Where the endoscope or other items to be cleaned are contaminated or potentially contaminated with Prions (proteinaceous infectious materials), the cleaning solution is preferably alkaline (preferably, pH 10 or above) and also contains surfactants for improving removal of these materials from the endoscope.

In an alternative embodiment, the cleaning concentrate is separately contained from the disinfectant concentrate/reagents. For example, the cleaning concentrate may be measured into a drawer in the reprocessor into which water is flowed or dispensed from a multi-dose dispenser 262 (FIG. 17).

In yet another embodiment, the base of the cartridge is formed from a porous material, which allows the water and solutions to pass through.

As best shown in FIGS. 1 and 17, a heater 264 situated in the fluid distribution system 165 heats the circulating liquid to a desired temperature for effective cleaning or disinfection. A preferred temperature is about 45–55 C., most preferably, about 48 C. for peracetic acid disinfection. The fluid distribution system 165 returns the sprayed liquid and the liquid which has passed through the head receiving container from the sump 221 to the upper spray head directly and to the endoscope container 16 and lower spray head via the manifold 163. At least a portion of the sprayed liquid is directed from the manifold 163 to the cartridge holder 210. This ensures thorough mixing of the treatment materials in the liquid and dissolution of any solid components before returning the liquid to the nozzles 168 and head-receiving container 16, 16'.

Preferably, as shown in FIG. 17, the incoming water is passed through a micro porous filter 265 in a water inlet line 266, which filters out particles of dirt and microorganisms. A valve 268 in the water inlet line 266 closes when the desired quantity of water has been admitted.

A typical cleaning and disinfection cycle proceeds as follows. A single use cartridge 212 is positioned in the cartridge holder 210 and the holder lid 222 closed and clamped. The head 22 of an endoscope to be cleaned is positioned in one of the head container portions 24, 26 with its insertion tube 62 extending into the tube 60 and its control cable 82 extending along the channel 88 of the lower housing portion 26. The head container 16, 16' is closed and the overcenter clamps 34 are then locked to bring the seals 108, 110, 116, into sealing relation with corresponding grooves 100, 102, 118. The rack 12 is mounted on wheels 270 to roll into and out of the reprocessor on tracks 272 adjacent sides of the chamber 14 (not shown). The hose 162 is connected to the manifold 163 via the outlet 164, for example, with a press fit connection. Other items to be cleaned are placed in the basket 85 of the rack 12. A door 276 to the reprocessor 10 is closed to seal an access opening 278 to the reprocessor chamber 14 (FIG. 17). During loading of the rack 12, it rests on the opened door 276.

The cleaning/disinfection cycle may include a pre-cleaning step, a cleaning/disinfection step, and one or more rinse steps. In the pre-cleaning step, clean water is introduced to the reprocessor and circulated to the nozzles 168 on the spray bars 169, 169' for spraying over exterior surfaces of items to be cleaned, and to the housing 20, for cleaning the endoscope head 22 and interior lumens of gross debris. After a period of recirculation sufficient to effect removal of most of the loose soil on the endoscope and other items being cleaned, a drain valve 290 associated with the sump 221 is opened and the pre-cleaning liquid allowed to flow into a drain line 292. The drain valve is then closed. Optionally, a detergent is added to the water for the pre-cleaning step.

Fresh water is then introduced to the reprocessor and is heated to 45–60° C. by the heater 264. The heated water is mixed with the concentrated cleaner/disinfectant or reagents to form a cleaning and disinfectant solution. The solution is circulated through the distribution system to the nozzles 168 and the head containers for sufficient time to disinfect the exterior and interior surfaces of the endoscopes and to disinfect other items in the reprocessor. The drain valve 290 in the sump is opened once more and the disinfectant solution allowed to flow into the drain line 292.

Fresh water is then introduced to the reprocessor to rinse the endoscope and other items. The water for this step is preferably purified, to reduce the chance for recontamination. For example, heat sterilized, micro-filtered, distilled, deionized, or other purified water is used for the rinse step. Optionally, the rinse water is mixed with a volatile agent, such as alcohol, to promote water removal. Finally, an air drying cycle is employed. With reference to FIG. 1, fresh air is directed by a fan 294 into the chamber and is also passed directly into the endoscope head containers 16, 16' to blow remaining liquid from the lumens of the endoscope. Preferably, the entering air or other drying gas is passed through a filter, such as a HEPA filter 296, to remove unwanted particles and microorganisms. The air may be heated to speed drying, although not above a temperature which could cause damage to the endoscope.

Other steps are optionally included in the cycle, or one or more of the steps eliminated or combined. For example, separate cleaning and disinfection steps may be performed, for example, by including separate compartments in the cup which are selectively opened to release first the cleaner concentrate and, subsequently, the disinfectant concentrate. Alternatively, one or other of the concentrates is contained elsewhere in the reprocessor. One or more leak testing steps are optionally included. For example, the endoscope is leak tested prior to being placed in the head container 16, 16' to ensure that the lumens which are intended to be leak tight do not permit water to enter and cause damage to sensitive components during reprocessing. Alternatively, a leak testing step may be carried out after positioning the endoscope head in the container 16, 16', either before or after inserting the container into the reprocessor chamber 14. A further leak test may be carried out after reprocessing to ensure that the endoscope has not been damaged during reprocessing.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for reprocessing a medical device having a tubular member with a lumen, the system comprising:
   a container which defines a pressure chamber into which a portion of the medical device is inserted, the container including:
      a first container portion which defines a first portion of the pressure chamber and a first channel,
      a second container portion which defines a second portion of the chamber and a second channel, the first and second channels together forming an outlet from the pressure chamber when the container portions are in a closed position, the outlet receiving the tubular member of the medical device therethrough, and
      a plurality of flexible fins longitudinally spaced along the first and second channels, which receive the tubular member therethrough, the fins permitting a restricted flow of reprocessing liquid through the pressure chamber outlet between the tubular member and the fins when the tubular member is received therein; and
   a pump which supplies pressurized reprocessing liquid to the pressure chamber such that the reprocessing liquid flows through the lumen and between the tubular member and the fins.

2. A reprocessing system for a device having a tubular member with a lumen, the system comprising:
   a container which defines a pressure chamber into which a portion of the device is inserted, the container including:

a first container portion which defines a first portion of the pressure chamber and a first channel, a second container portion which defines a second portion of the chamber and a second channel, the first and second channels together forming an outlet from the pressure chamber when the container portions are in a closed position, the outlet receiving the tubular member of the device therethrough, and a flexing gasket assembly associated with the first and second channels which defines a plurality of longitudinally spaced openings when the container portions are in a closed position, the openings permitting a restricted flow of reprocessing liquid through the pressure chamber outlet between the tubular member and the flexing gasket assembly when the tubular member is received therein; and a pump which supplies pressurized reprocessing liquid to the pressure chamber such that the reprocessing liquid flows through the lumen and between the tubular member and the flexing gasket.

3. The system of claim 2, wherein the gasket assembly includes a plurality of fins which extend into the outlet, each of the fins defining a slot for receiving the tubular member therethrough.

4. The system of claim 3, wherein a first plurality of the fins is associated with the first channel and a second plurality of the fins is associated with the second channel.

5. The system of claim 4, wherein the first and second pluralities of the fins meet such that pairs of slots define the openings for receiving the tubular member therethrough.

6. The system of claim 5, wherein the openings vary in size along the outlet.

7. The system of claim 6, wherein the openings diminish in size from an end of the outlet proximal the pressure chamber.

8. The system of claim 1, wherein the fins are curved with a midpoint of each fin being downstream of edges of the fin.

9. The system of claim 8, wherein a slot is formed at the midpoint.

10. The system of claim 1, wherein the fins include a base portion and a rib portion, the rib portion extending into the outlet.

11. The system of claim 10, wherein a plurality of the base portions are connected together to define a first gasket portion.

12. The system of claim 9, wherein the first gasket portion is seated in the first channel and a second gasket portion is seated in the second channel.

13. The system of claim 1, wherein the fins are generally U-shaped and taper outward from the container.

14. The system of claim 1, further including a tube connected with an opening in one of the first container portion and the second container portion for receiving a second tubular member of the medical device therein.

15. A reprocessing system of for a device having a first tubular member with a lumen, the system comprising:

a container which defines a pressure chamber into which a portion of the device is inserted, the container including:

a first container portion which defines a first portion of the pressure chamber and a first channel, a second container portion which defines a second portion of the chamber and a second channel, the first and second channels together forming a first outlet from the pressure chamber when the container portions are in a closed position, the outlet receiving the first tubular member of the device therethrough, a flexing gasket assembly which permits a restricted flow of reprocessing liquid through the pressure chamber outlet between the first tubular member and the flexing gasket assembly when the first tubular member is received therein, and a tube connected with a second opening in one of the first container portion and the second container portion for receiving a second tubular member of the device therein, a restrictor positioned in the tube or second opening for providing a restricted flow of liquid between the tube and the second tubular member; and a pump which supplies pressurized reprocessing liquid to the pressure chamber such that the reprocessing liquid flows through the lumen and between the first tubular member and the flexing gasket and between the tube and the second tubular member.

16. The system of claim 15, wherein the restrictor includes a flexible gasket with a conical portion.

17. The system of claim 1, further including a cartridge holder for selectively receiving a cartridge containing a reprocessing concentrate.

18. The system of claim 17, wherein the cartridge holder is mounted to a rack assembly which also supports the container.

19. A system for reprocessing a medical device having a tubular member with a lumen, the system comprising:

a container which defines a pressure chamber into which a portion of the medical device is inserted, the container including:

a first container portion which defines a first portion of the pressure chamber and a first channel.

a second container portion which defines a second portion of the chamber and a second channel, the first and second channels together forming an outlet from the pressure chamber when the container portions are in a closed position, the outlet receiving the tubular member of the medical device therethrough;

a pump which supplies pressurized reprocessing liquid to the pressure chamber such that the reprocessing liquid flows through the lumen and between the tubular member and the flexing gasket;

a rack which supports the container; and a cartridge holder supported by the rack for selectively receiving a cartridge containing a reprocessing concentrate, the cartridge holder including:

a cup receiving portion with a projection at a lower end thereof;

a pivotal top which presses a cup into the projection as the top is pivoted from an open position to a closed position; and a fluid inlet and a fluid outlet.

20. A system for reprocessing a medical device having a tubular member with a lumen, the system comprising:

a first container portion which defines a first portion of a pressure chamber into which a portion of the medical device is inserted and a first channel;

a second container portion which mates with the first container portion to close the pressure chamber, the second container portion defining a second channel that mates with the first channel to form an outlet from the pressure chamber, the outlet receiving the tubular member of the medical device therethrough an assembly which permits a restricted flow of reprocessing liquid through the pressure chamber outlet between the tubular member and the assembly;

a pump which supplies pressurized reprocessing liquid to the pressure chamber such that the reprocessing liquid flows through the lumen and between the tubular member and the assembly; and an indicator holder, carried by the container for selectively receiving an indicator, the indicator being one which exhibits a detectable change in response to exposure to the reprocessing liquid, the holder including a bore having openings at first and second ends such that reprocessing fluid enters the bore through one of the openings, contacts the indicator and flows out of the bore through the second opening.

21. The system of claim 20, wherein the indicator is in the form of a strip which carries at least one of a chemical indicator material and a biological indicator material thereon.

22. The A system for reprocessing a medical device having a tubular member with a lumen, the system comprising:

a container which defines a pressure chamber into which a portion of the medical device is inserted, the container including:

first container portion which defines a first portion of the pressure chamber and a first channel, a second container portion which defines a second portion of the chamber and a second channel, the first and second channels together forming an outlet from the pressure chamber when the container portions are in a closed position, the outlet receiving the tubular member of the medical device therethrough, and a flexing gasket assembly which permits a restricted flow of reprocessing liquid through the pressure chamber outlet between the tubular member and the flexing gasket assembly when the tubular member is received therein;

a pump which supplies pressurized reprocessing liquid to the pressure chamber such that the reprocessing liquid flows through the lumen and between the tubular member and the flexing gasket; and an indicator holder, carried by the container and including a bore for selectively receiving an indicator on a strip, the indicator being one which exhibits a detectable change in response to exposure to the reprocessing liquid, the holder including a clip, mounted to the container, for restraining an upper end of the indicator strip, the indicator being disposed on a portion of the strip within the bore.

23. A method for reprocessing an endoscope comprising:

positioning the endoscope such that a head of the endoscope is received in a pressure chamber defined by first and second container portions and a tubular member of the endoscope extends through an outlet to the pressure chamber;

flowing a reprocessing liquid into the chamber and out of the chamber via a lumen in the tubular member and between the outlet and the tubular member;

restricting liquid flow between the outlet and the tubular member with a plurality of longitudinally spaced resiliently flexible fins.

24. The method of claim 23, wherein the step of positioning the endoscope includes:

positioning the endoscope head in the first container with the tubular member extending through a first channel which extends from the container portion, a first plurality of the fins being disposed in the first channel;

closing the second container portion over the first container portion to form the chamber, a second channel extending from the second container portion a second plurality of the fins being disposed in the second channel, the first and second channels forming the outlet therebetween, the first and second pluralities of the fins overlapping to define a plurality of openings which are generally axially aligned in the outlet.

25. The method of claim 23, wherein the container has a second outlet and the endoscope includes a second tubular member, the method further including:

inserting the second tubular member through a flexible gasket having a conical portion in the second outlet; and restricting liquid flow between the second outlet and the second tubular member with the gasket.

26. The method of claim 23, wherein the step of flowing a reprocessing liquid includes:

flowing water through a cartridge, the water mixing with a concentrated source of reprocessing liquid in the cartridge to form the reprocessing liquid.

27. The method of claim 23, wherein the reprocessing liquid includes peracetic acid.

28. The method of claim 23, wherein the step of flowing a reprocessing liquid into the chamber includes:

flowing a first reprocessing liquid into the chamber which includes an alkaline cleaning solution which removes prions;

draining the first reprocessing liquid from the chamber; and flowing a microbial decontaminant into the chamber which destroys prions.

29. A container for receiving an endoscope head, the container comprising:

a chamber which receives the endoscope head;

a tube extending from the chamber for receiving an insertion tube of the endoscope;

an outlet from the chamber for receiving a connector cord; and a plurality of fins longitudinally spaced along the outlet, the fins each including:

a base portion selectively connected to the outlet, and a rib which extends from the base, the rib defining a slot for receiving the connector cord therethrough, the slots of the respective ribs decreasing in size from a distal end to an outlet end of the outlet.

30. The container of claim 29, wherein the container includes:

a first housing portion which defines a first portion of the outlet, a first plurality of the fins being connected to the first portion of the outlet; and a second housing portion which defines a second portion of the outlet, a second plurality of the fins being connected to the second portion of the outlet, such that pairs of ribs overlap, slots on the overlapping ribs together defining an opening.

31. The container of claim 29, further including:

a gasket having a conical portion at an entrance to the tube through which the insertion tube is inserted.

32. The container of claim 30, wherein the fins are each u-shaped and tapered.

33. The container of claim 29, further including:

an indicator holder, carried by the container, for selectively receiving an indicator, the indicator being one which exhibits a detectable change in response to exposure to a reprocessing liquid.

34. A system for reprocessing a medical device comprising:
- a reprocessing chamber;
- a container received by the reprocessing chamber which defines an interior chamber for selectively receiving at least a portion of the medical device;
- a pump which supplies a reprocessing liquid to the interior chamber to contact surfaces of the device, the reprocessing liquid flowing from the container into the reprocessing chamber; and
- an indicator holder, carried by an exterior of the container, for selectively receiving an indicator, the indicator exhibiting a detectable change in response to exposure to the reprocessing liquid exterior to the container, within the reprocessing chamber.

35. A system for reprocessing a medical device comprising:
- a reprocessing chamber;
- a container received by the reprocessing chamber which defines an interior chamber for selectively receiving at least a portion of the medical device;
- a pump which supplies a reprocessing liquid to the interior chamber to contact surfaces of the device; and
- an indicator holder, carried by the container, for selectively receiving an indicator, the indicator exhibiting a detectable change in response to exposure to the reprocessing liquid, the indicator holder including a block which extends from an exterior surface of the container, the block defining a bore for receiving the indicator, the bore having openings, at first and second ends such that reprocessing fluid enters the bore through one of the openings, contacts the indicator and flows out of the bore through the second opening.

36. The system of claim 35, wherein the indicator holder further includes a clip for selectively engaging a first portion of the indicator, such that a second portion of the indicator is disposed in the bore, the second portion carrying at least one of a chemical indicator material and a biological indicator material.

* * * * *

UNITED STATES PATENT AND TRADEMARK OFFICE
CERTIFICATE OF CORRECTION

PATENT NO. : 6,919,057 B2  
DATED : July 19, 2005  
INVENTOR(S) : Halstead et al.

It is certified that error appears in the above-identified patent and that said Letters Patent is hereby corrected as shown below:

<u>Title page,</u>
Item [75], Inventors, please add -- Herbert J Kaiser, Pontoon Beach, IL. -- after "Maxime Nicole, St. Pacome (CA)".

Signed and Sealed this

Twenty-ninth Day of November, 2005

JON W. DUDAS
*Director of the United States Patent and Trademark Office*